US011311251B2

(12) United States Patent
Goto et al.

(10) Patent No.: US 11,311,251 B2
(45) Date of Patent: Apr. 26, 2022

(54) EXERCISE SUPPORT APPARATUS

(71) Applicant: Nikkiso Company Limited, Tokyo (JP)

(72) Inventors: Hitoshi Goto, Shizuoka (JP); Kunihiko Akita, Shizuoka (JP); Nobuhiko Aida, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 280 days.

(21) Appl. No.: 16/419,239

(22) Filed: May 22, 2019

(65) Prior Publication Data

US 2019/0274639 A1   Sep. 12, 2019

Related U.S. Application Data

(63) Continuation of application No. PCT/JP2017/042666, filed on Nov. 28, 2017.

(30) Foreign Application Priority Data

Nov. 28, 2016 (JP) .............................. JP2016-229625
Dec. 6, 2016 (JP) .............................. JP2016-236869
Dec. 6, 2016 (JP) .............................. JP2016-236870

(51) Int. Cl.
*A61B 5/00* (2006.01)
*A61B 5/021* (2006.01)
(Continued)

(52) U.S. Cl.
CPC .............. *A61B 5/746* (2013.01); *A61B 5/021* (2013.01); *A61B 5/6866* (2013.01); *A61M 1/16* (2013.01);
(Continued)

(58) Field of Classification Search
CPC ....... A61B 5/746; A61B 5/021; A61B 5/0002; A61B 5/14542; A61B 5/026;
(Continued)

(56) References Cited

U.S. PATENT DOCUMENTS 5,738,612 A * 4/1998 Tsuda ................. A61B 5/02225
                                                    482/5
7,785,463 B2 * 8/2010 Bissler ................ A61M 1/1613
                                                    604/4.01
(Continued)

FOREIGN PATENT DOCUMENTS

JP   2016-129624   7/2016
WO   1988/005667   8/1988
(Continued)

OTHER PUBLICATIONS

I. Jeong and J. Finkelstein, "Interactive biking exercise (iBikE) platform to facilitate lower extremity cycling exercise: System design and feasibility," 2012 5th International Conference on BioMedical Engineering and Informatics, 2012, pp. 1091-1095, doi: 10.1109/BMEI.2012.6512946. (Year: 2012).*
(Continued)

*Primary Examiner* — Sean P Dougherty
*Assistant Examiner* — Kyle W. Kretzer
(74) *Attorney, Agent, or Firm* — Young Basile Hanlon & MacFarlane, P.C.

(57) ABSTRACT

An exercise support apparatus is capable of supporting exercise taken by a patient during blood purification treatment and includes an estimation generating device that generates an estimation representing a circulating-blood-volume rate of change regarding a circulating blood volume that is estimated to be observed after the exercise is started, the estimation being generated after the blood purification treatment is started and from a continuous measurement of the circulating-blood-volume rate of change as regarding changes in circulating blood volume that is conducted before the exercise is started; a calculating device that calculates a difference between a measured value of the circulating-blood-volume rate of change that is acquired after the exercise during the blood purification treatment is started
(Continued)

and a value of the estimation generated by the estimation generating device; and a first monitoring device that monitors whether the difference or ratio calculated by the first calculating device is over a predetermined threshold.

18 Claims, 23 Drawing Sheets

(51) Int. Cl.
  *A63B 22/06* (2006.01)
  *A61M 1/14* (2006.01)
  *A61B 5/026* (2006.01)
  *A61M 1/16* (2006.01)

(52) U.S. Cl.
  CPC ........ *A63B 22/0605* (2013.01); *A61B 5/0002* (2013.01); *A61B 5/026* (2013.01); *A61M 1/14* (2013.01); *A61M 2205/502* (2013.01); *A61M 2205/52* (2013.01); *A63B 2022/0635* (2013.01); *A63B 2230/30* (2013.01)

(58) Field of Classification Search
  CPC .... A61B 5/02042; A61B 5/6866; A61M 1/16; A61M 1/14; A61M 1/3663; A61M 1/1615; A61M 2205/3331; A61M 2205/52; A61M 2205/502; A63B 22/0605; A63B 2022/0635; A63B 2230/30
  See application file for complete search history.

(56) References Cited

U.S. PATENT DOCUMENTS

2004/0238418 A1* 12/2004 Ikeda ................ A61M 1/36
  210/86
2006/0289342 A1* 12/2006 Sugioka ............ A61M 1/1615
  210/138

FOREIGN PATENT DOCUMENTS

| WO | 2007/014423 A1 | 2/2007 |
| WO | 2008/155077 A1 | 12/2008 |
| WO | 2009/024947 A2 | 2/2009 |

OTHER PUBLICATIONS

Gołęowski T, Kusztal M, Weyde W, Dziubek W, Woźniewski M, Madziarska K, Krajewska M, Letachowicz K, Strempska B, Klinger M: A Program of Physical Rehabilitation during Hemodialysis Sessions Improves the Fitness of Dialysis Patients. Kidney Blood Press Res 2012;35:290-296. doi: 10.1159/000335411 (Year: 2012).*
International Search Report from the Japanese Patent Office for Application No. PCT/JP2017/042666 dated Feb. 6, 2018.
Kohzuki, Masahiro, non-official translation (Pathophysiology and treatment 5, CKD and renal rehabilitation), Biomedicine & Therapeutics, 2010, vol. 44, No. 3, p. 63-68.
European Search Report for corresponding European Patent Application No. 17 873 751.6 dated Jul. 6, 2020.
Banerjee et al., "The haemodynamic response to submaximal exercise during isovolaemic haemodialysis", Nephrology Dialysis Transplantation, vol. 19, No. 6, pp. 1528-1532, May 18, 2004.

* cited by examiner

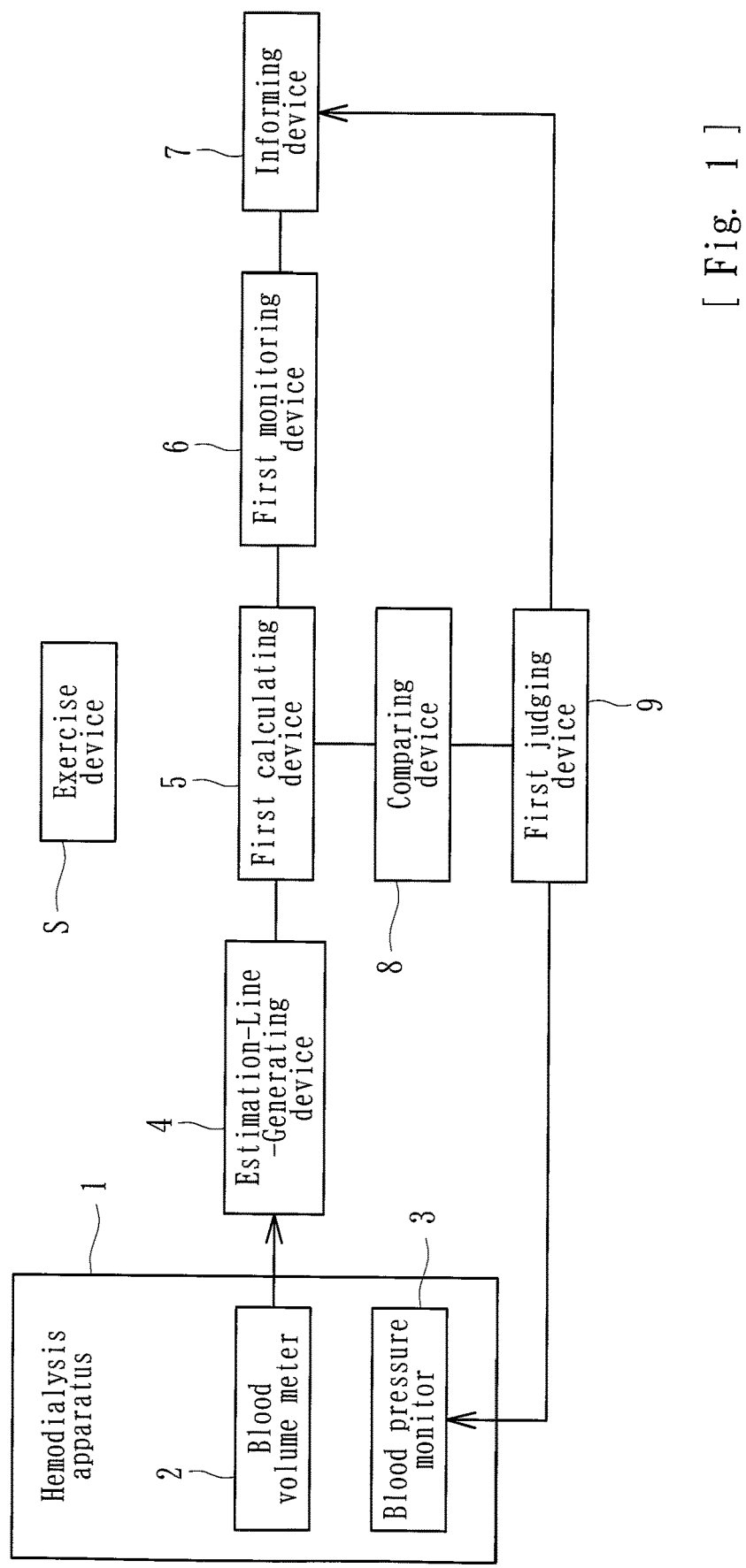
[Fig. 1]

[Fig. 2]
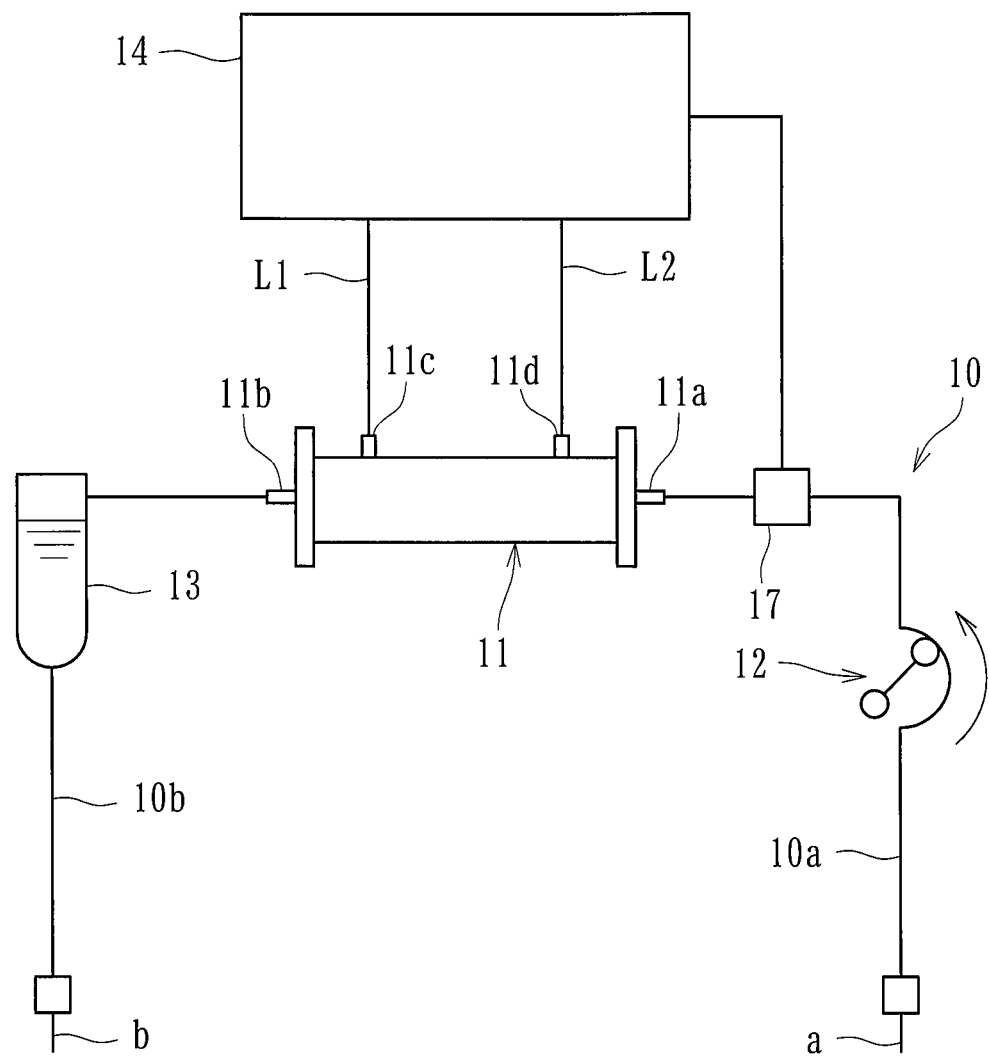

[Fig. 3]
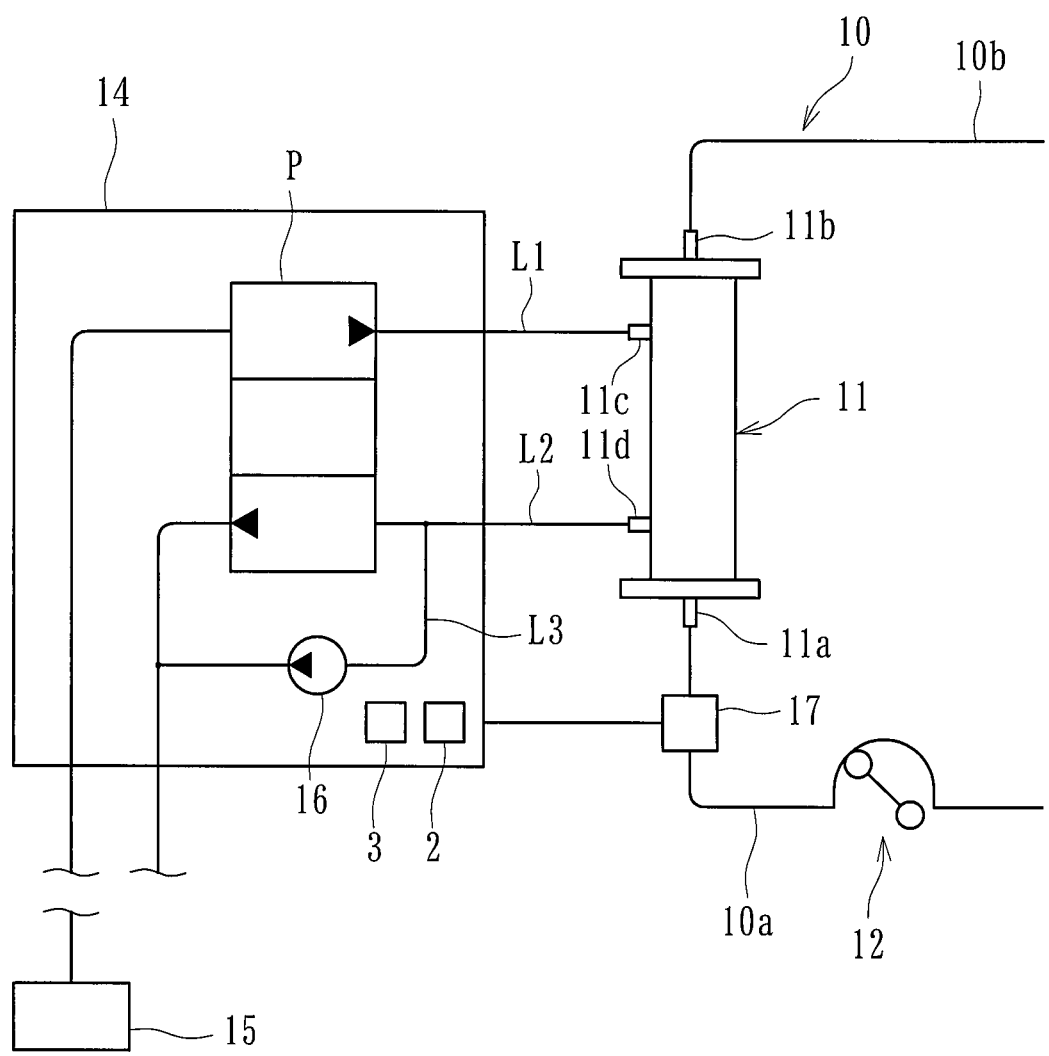

[Fig. 4]
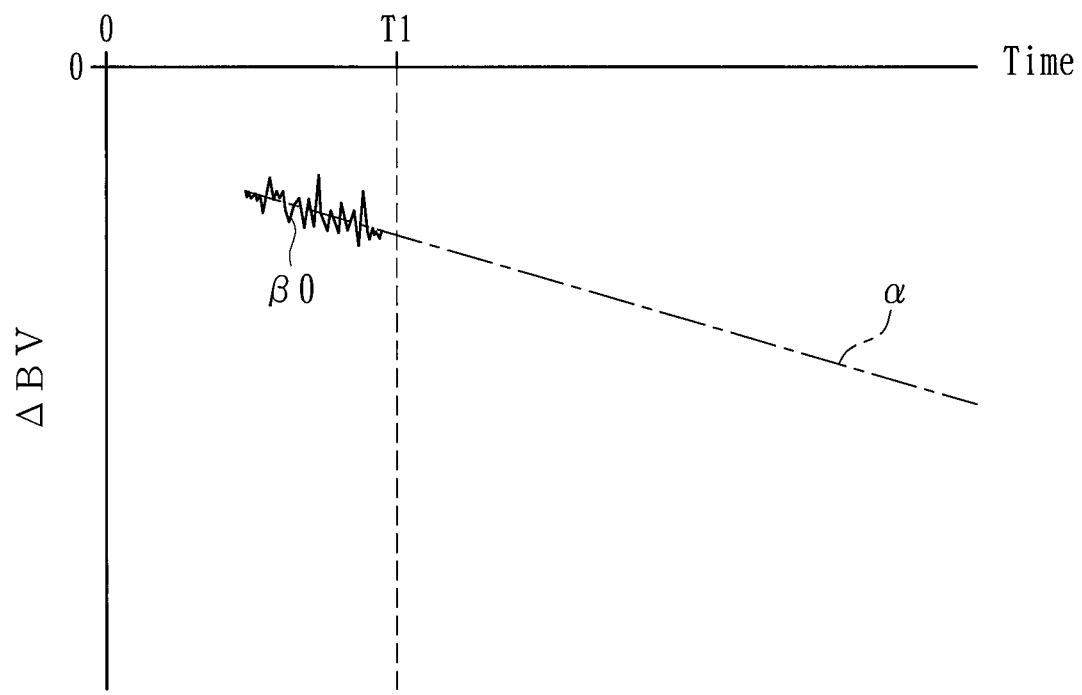

[Fig. 5]
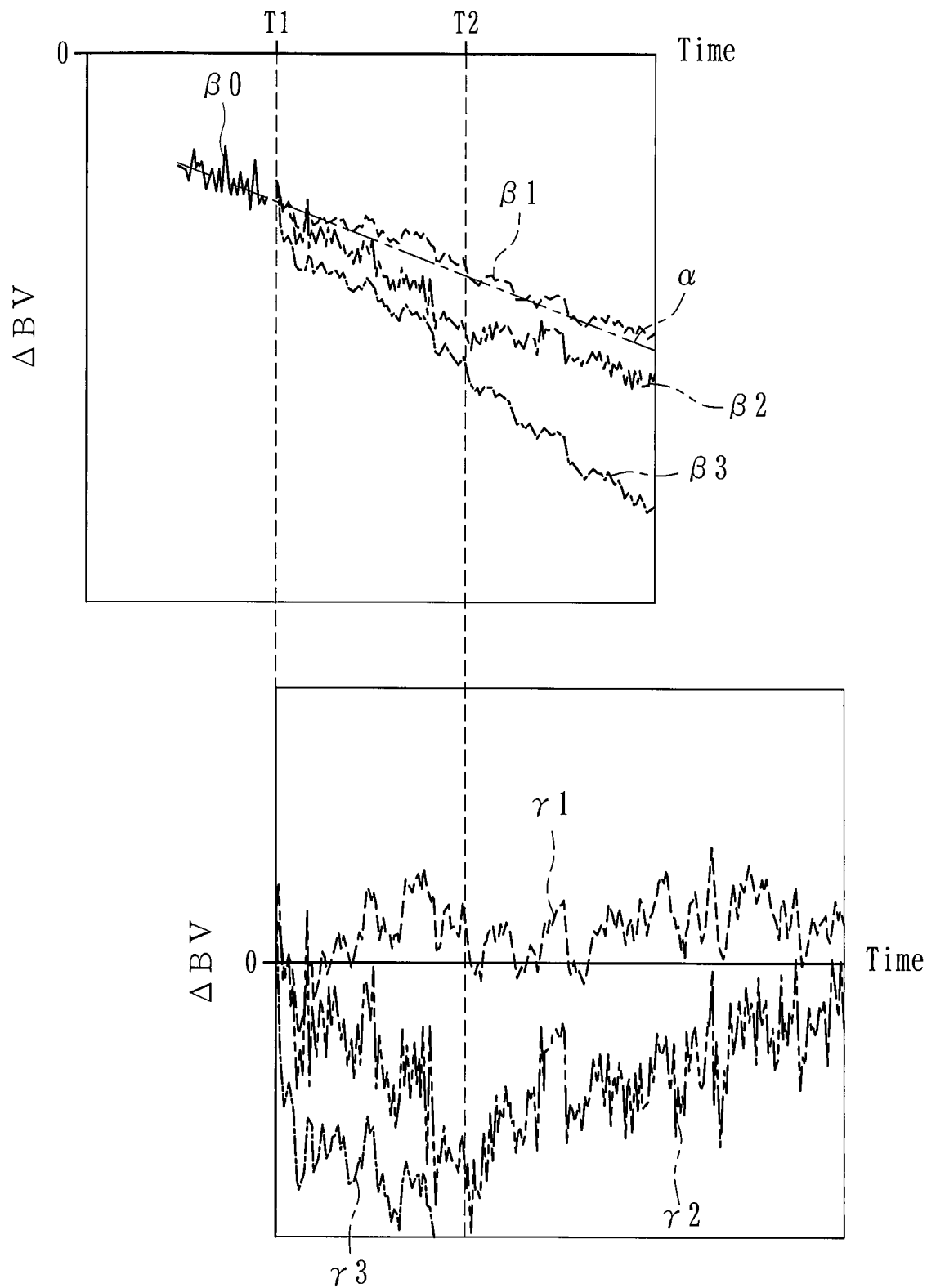

[ Fig. 6 ]
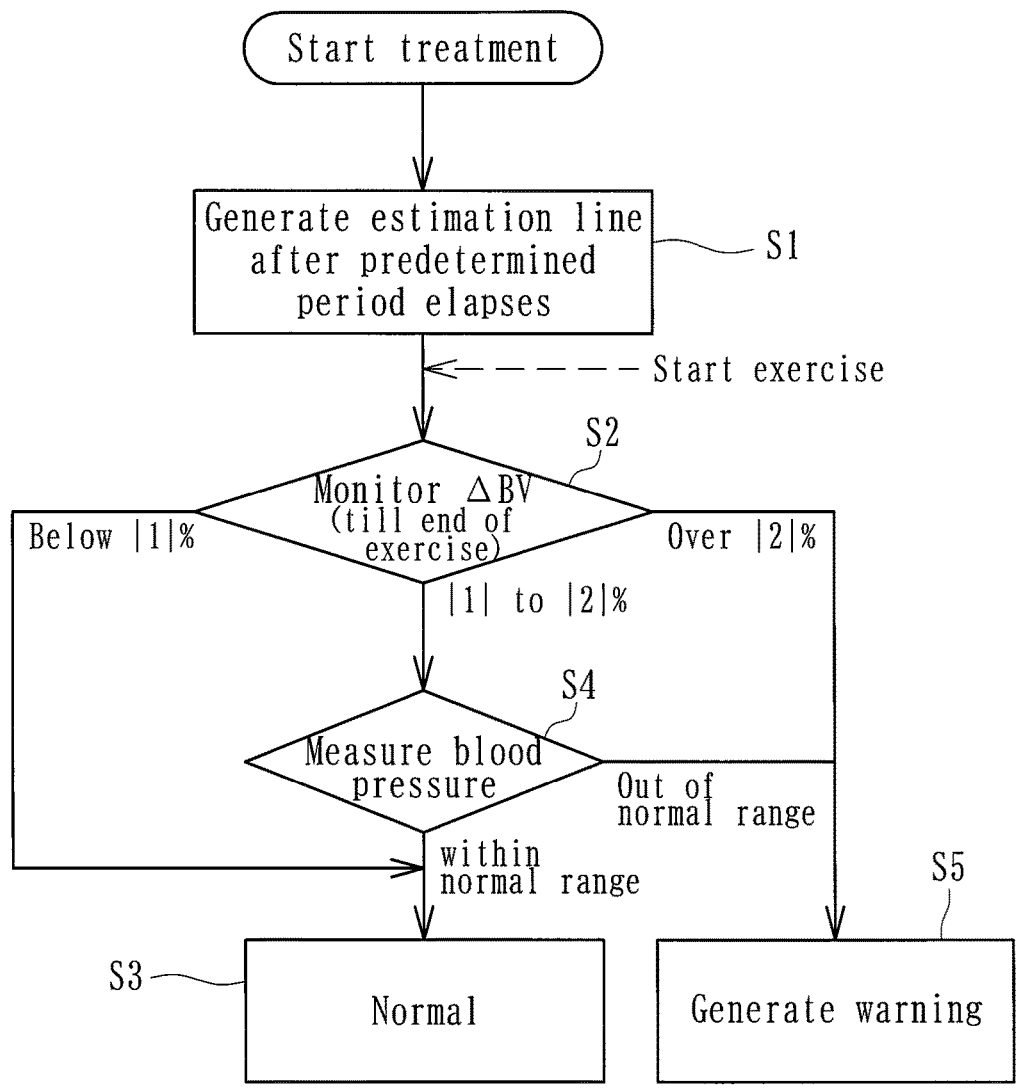

[Fig. 7]
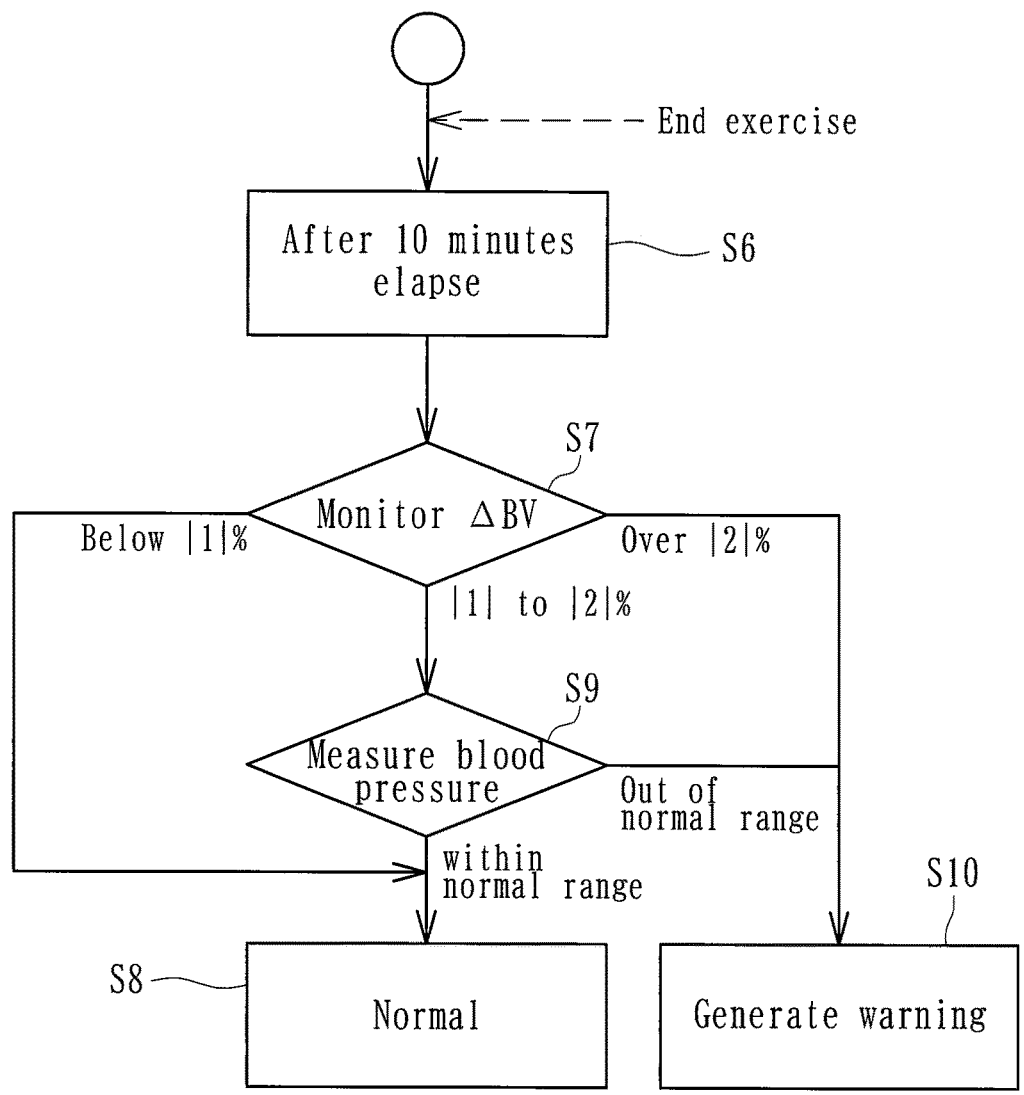

[Fig. 8]
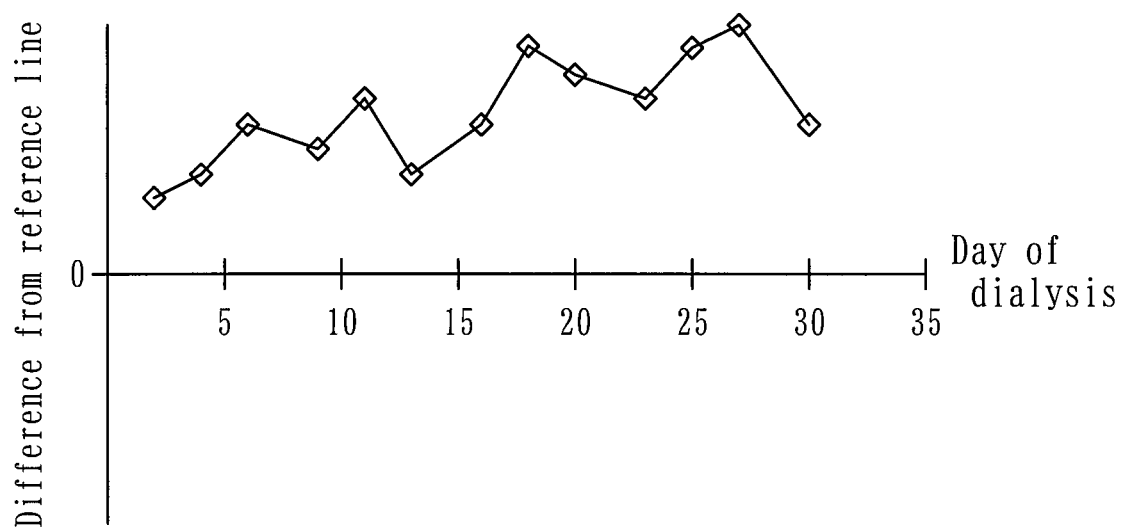

[Fig. 9]
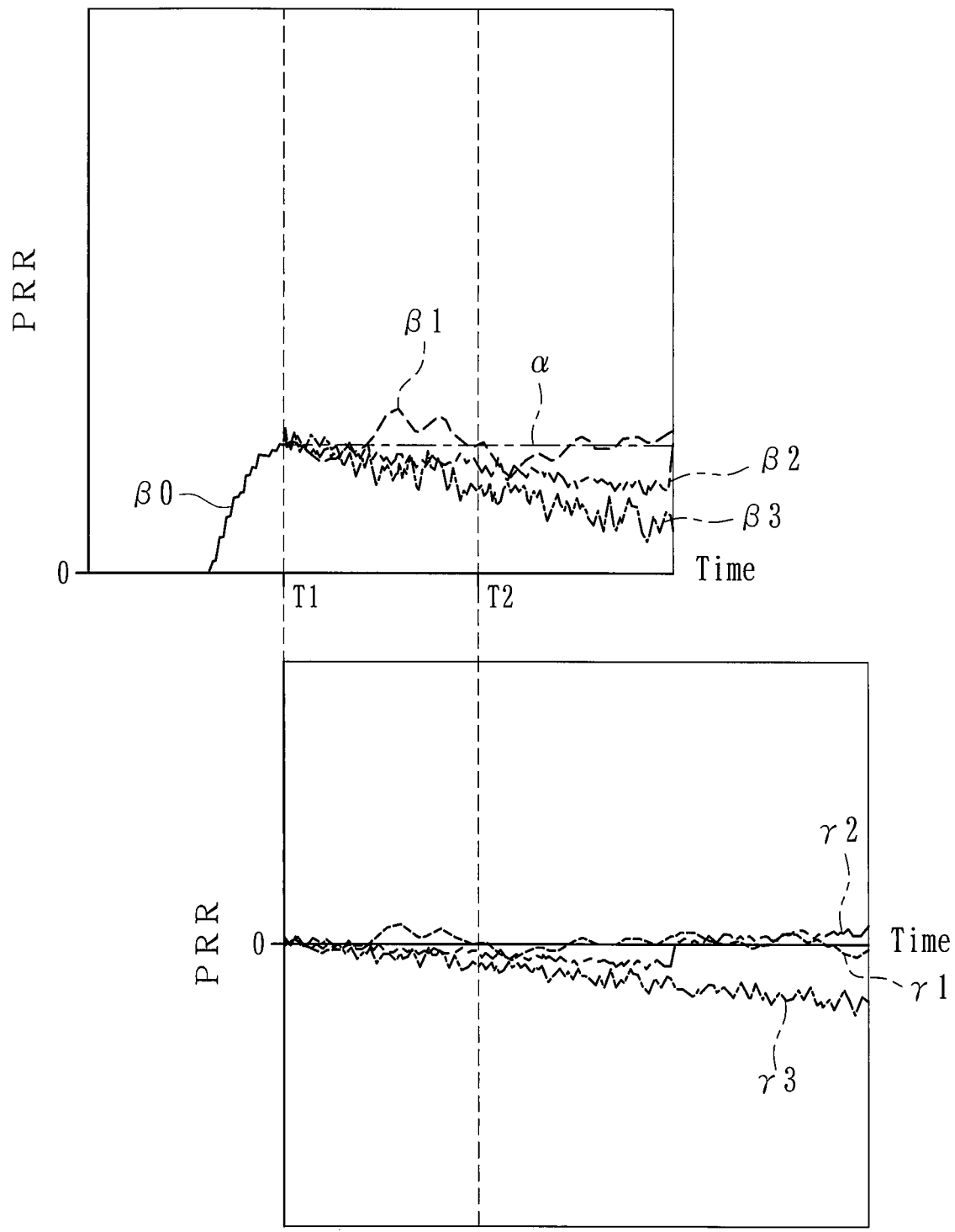

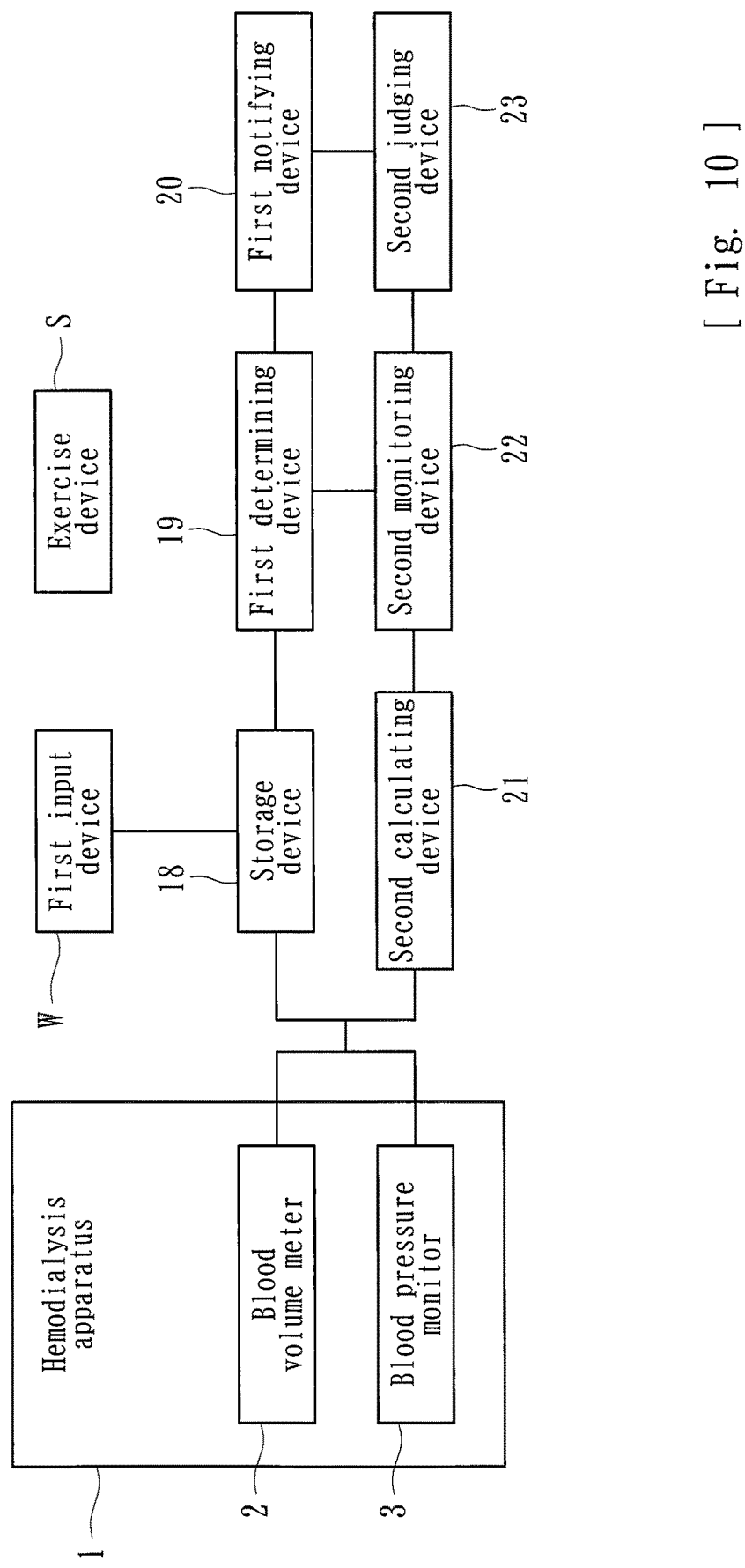
[Fig. 10]

[ Fig. 11 ]
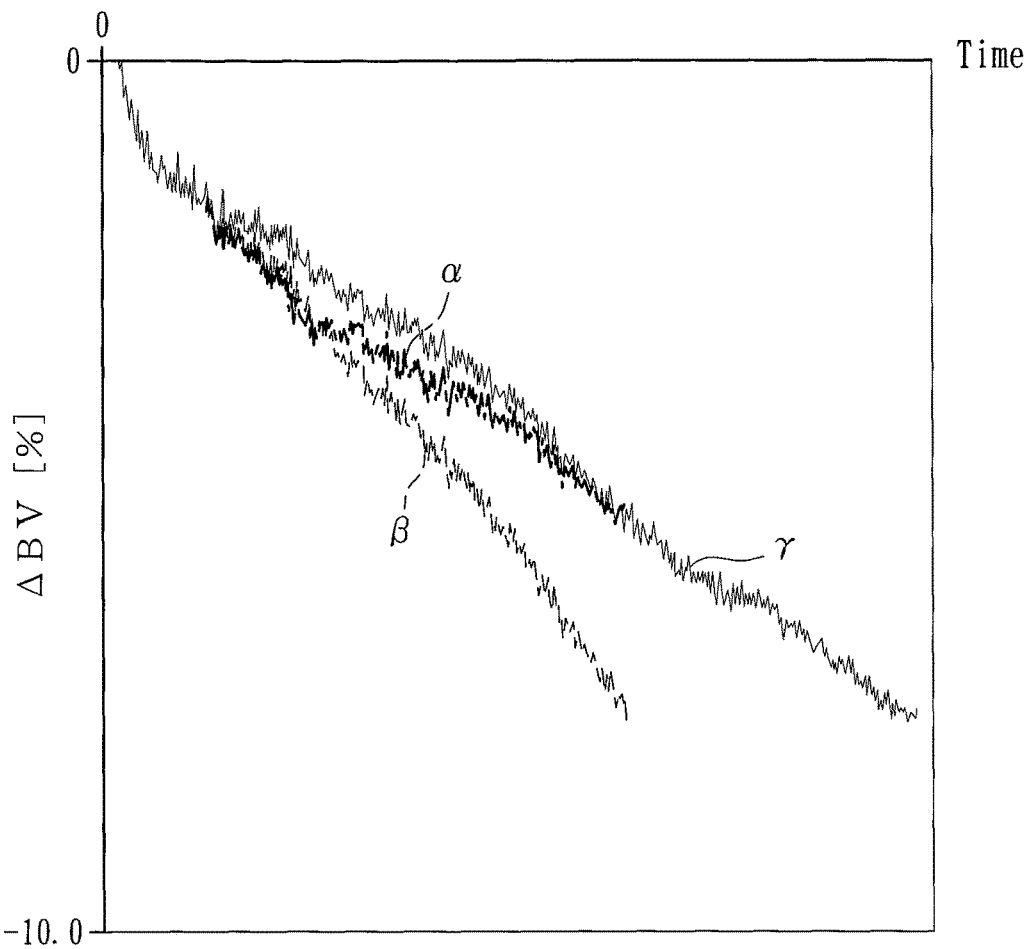
[ Fig. 12 ]
| Borg RPE Scale (Original Scale) | |
|---|---|
| 6 | |
| 7 | Very, very light |
| 8 | |
| 9 | Very light |
| 10 | |
| 11 | Fairly light |
| 12 | |
| 13 | Somewhat hard |
| 14 | |
| 15 | Hard |
| 16 | |
| 17 | Very hard |
| 18 | |
| 19 | Very, very hard |
| 20 | |
| Modified Borg Scale | |
|---|---|
| 0 | Nothing at all |
| 0.5 | Very weak |
| 1 | Very weak |
| 2 | Weak |
| 3 | |
| 4 | Somewhat strong |
| 5 | Strong |
| 6 | |
| 7 | Very strong |
| 8 | |
| 9 | |
| 10 | Very, very strong |

[Fig. 13]
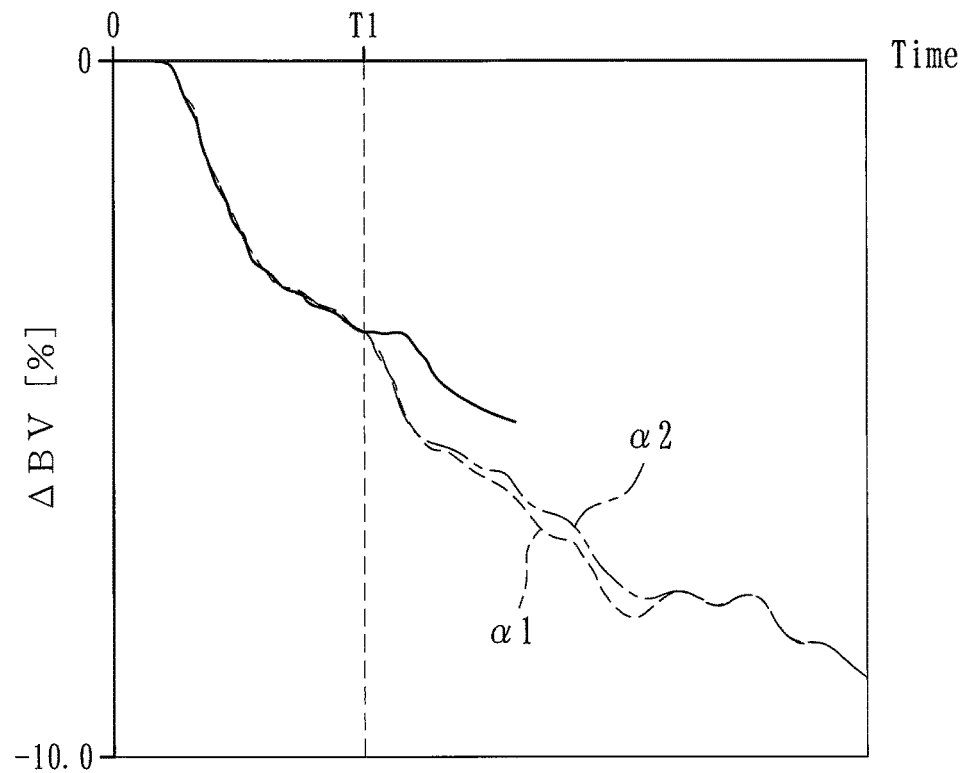
[Fig. 14]
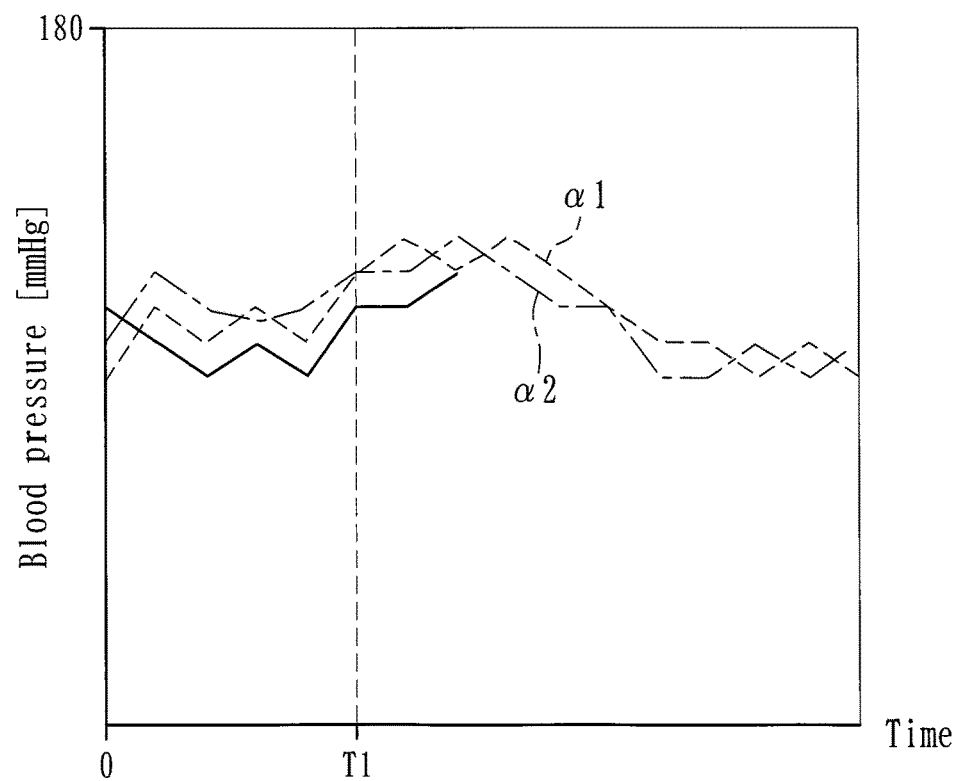

[Fig. 15]
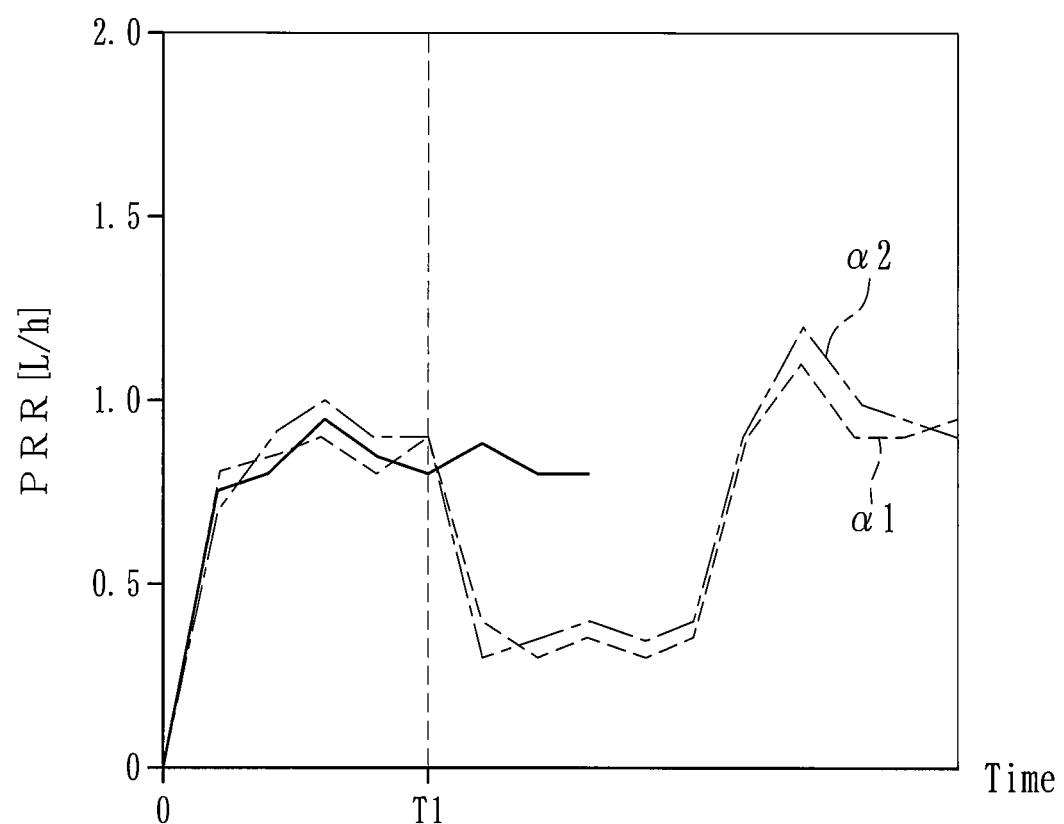

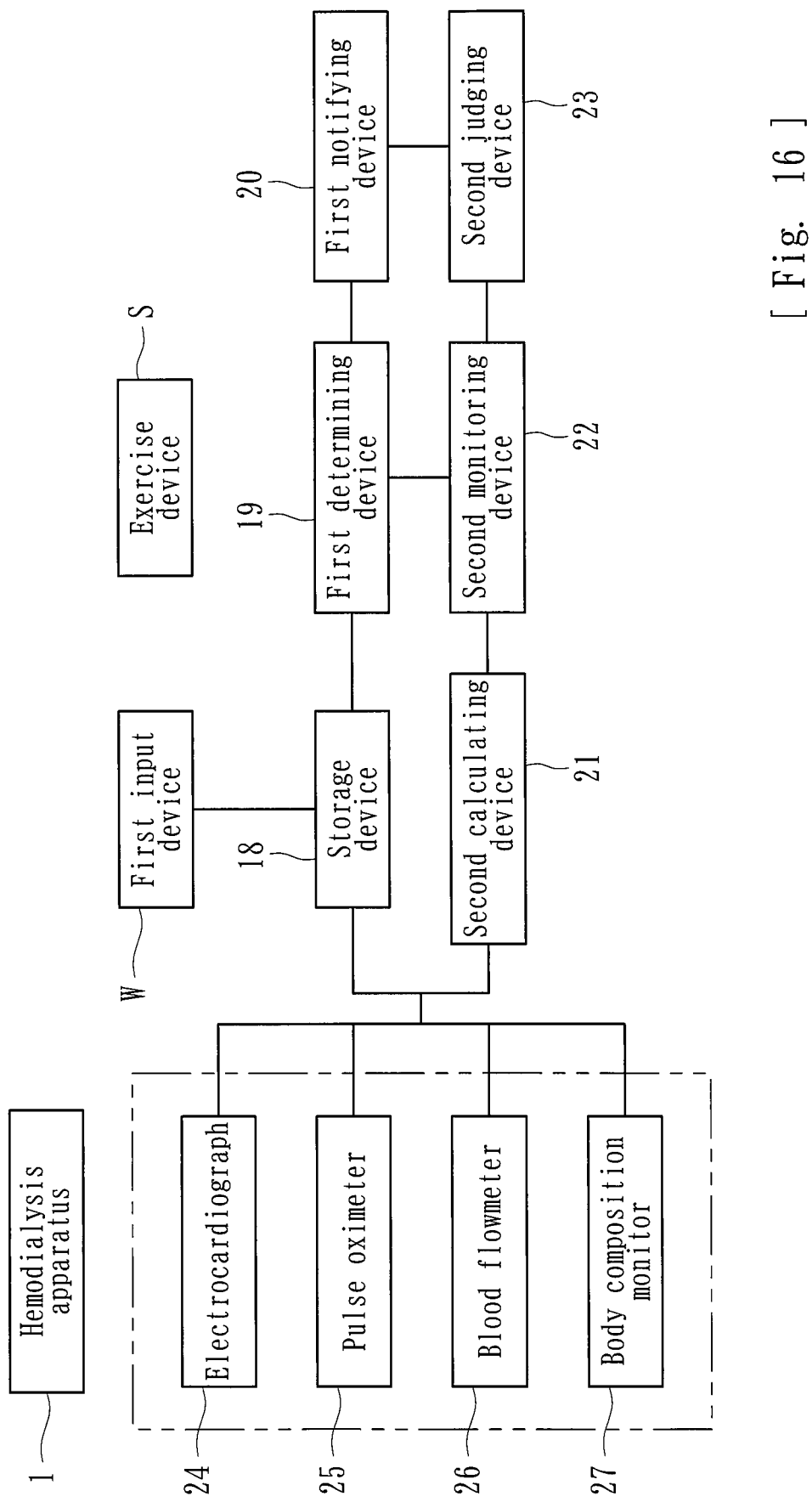
[ Fig. 16 ]

[Fig. 17]
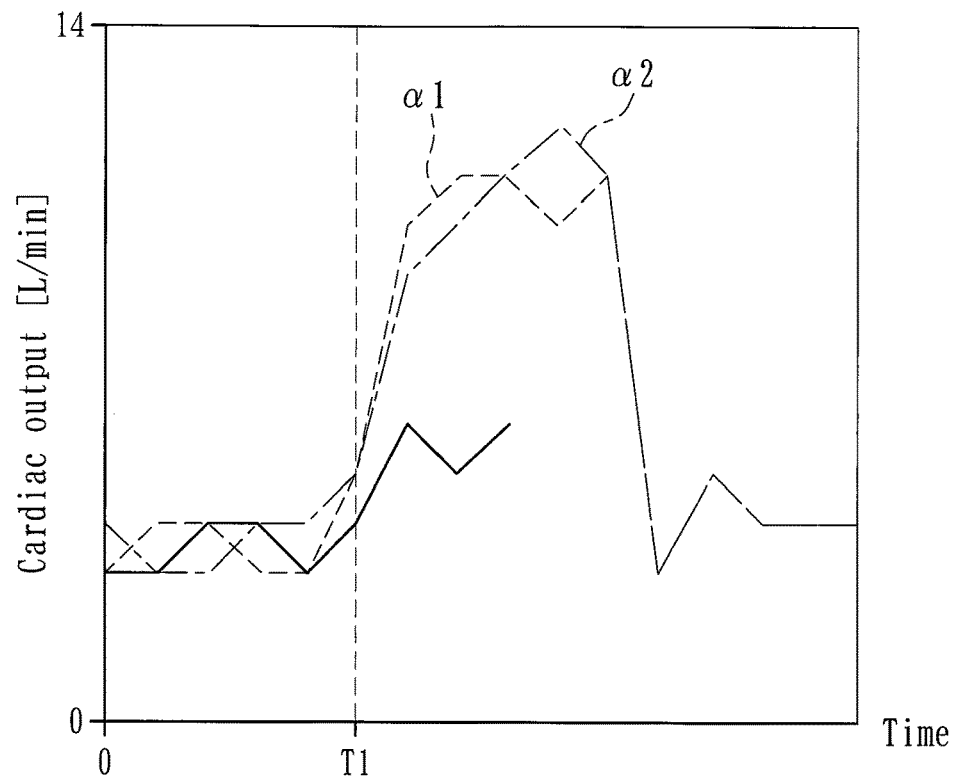
[Fig. 18]
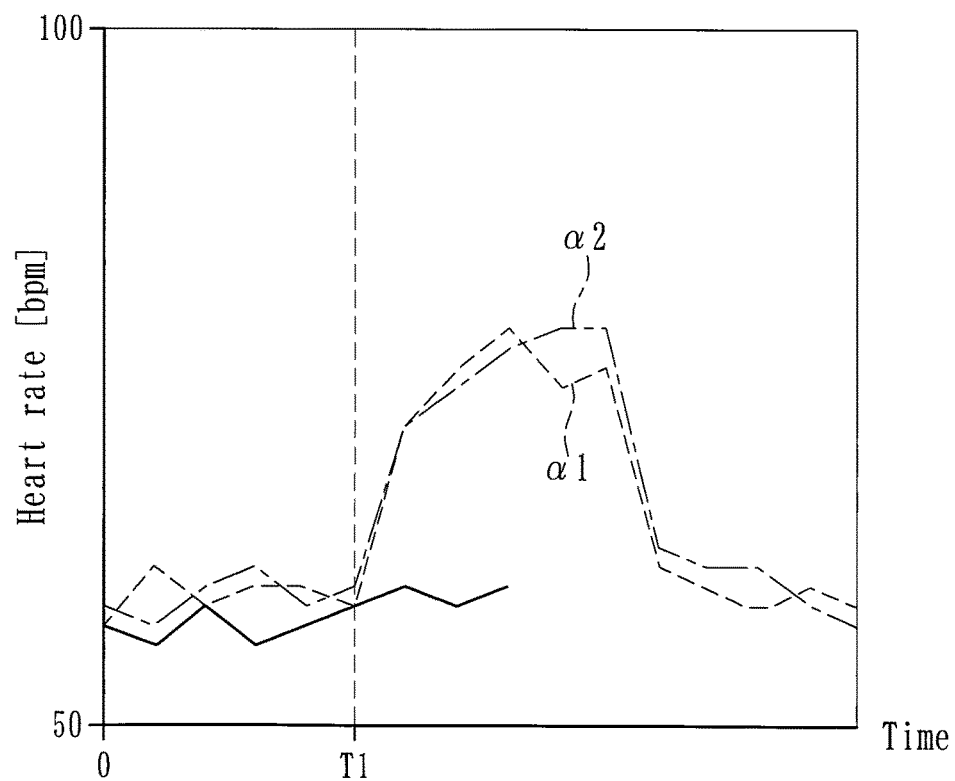

[ Fig. 19 ]
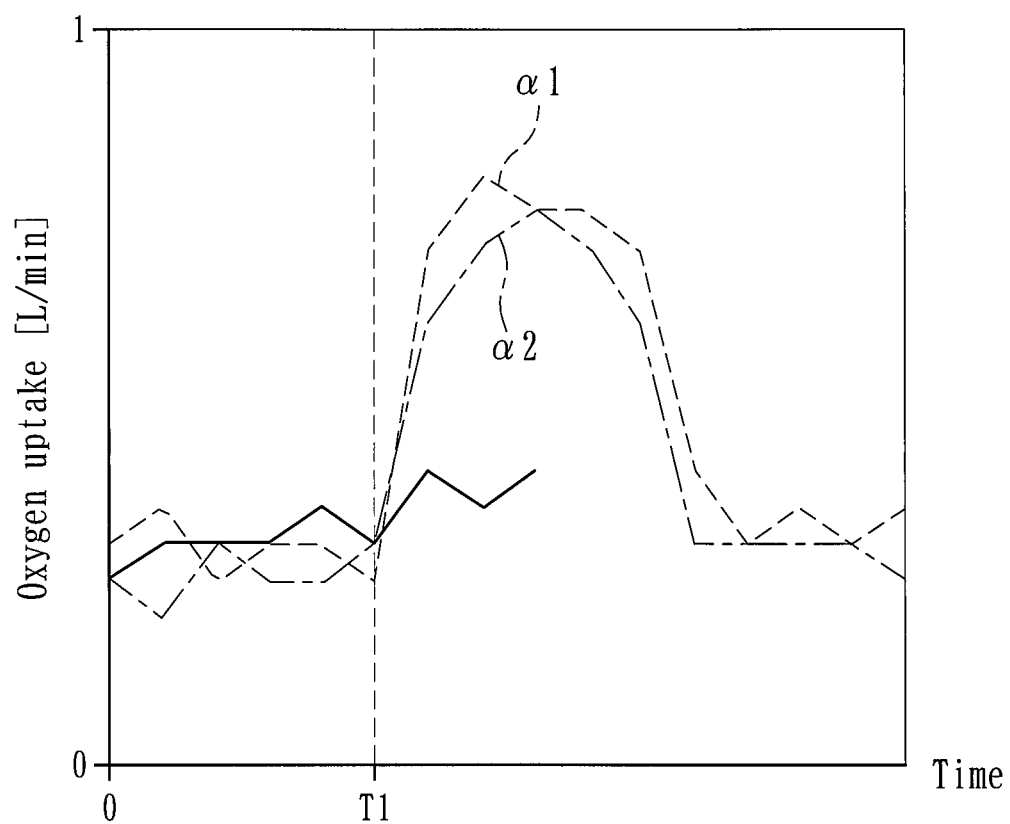

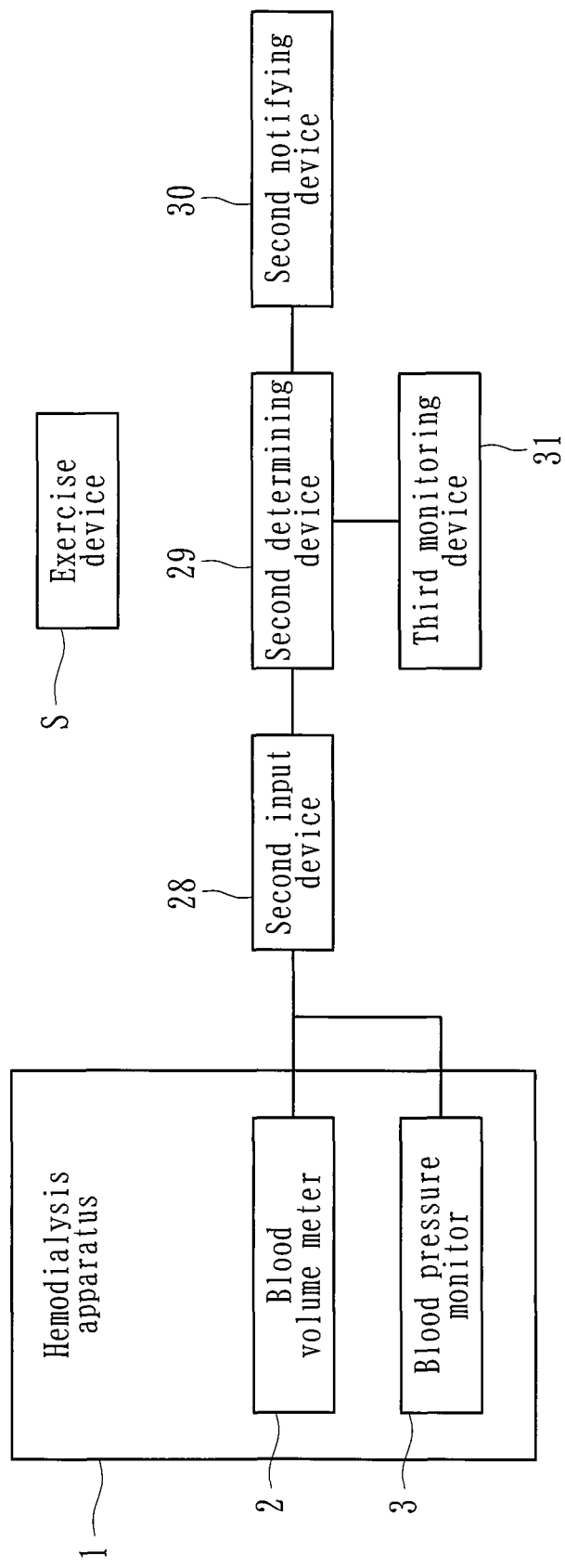
[Fig. 20]

[Fig. 21]
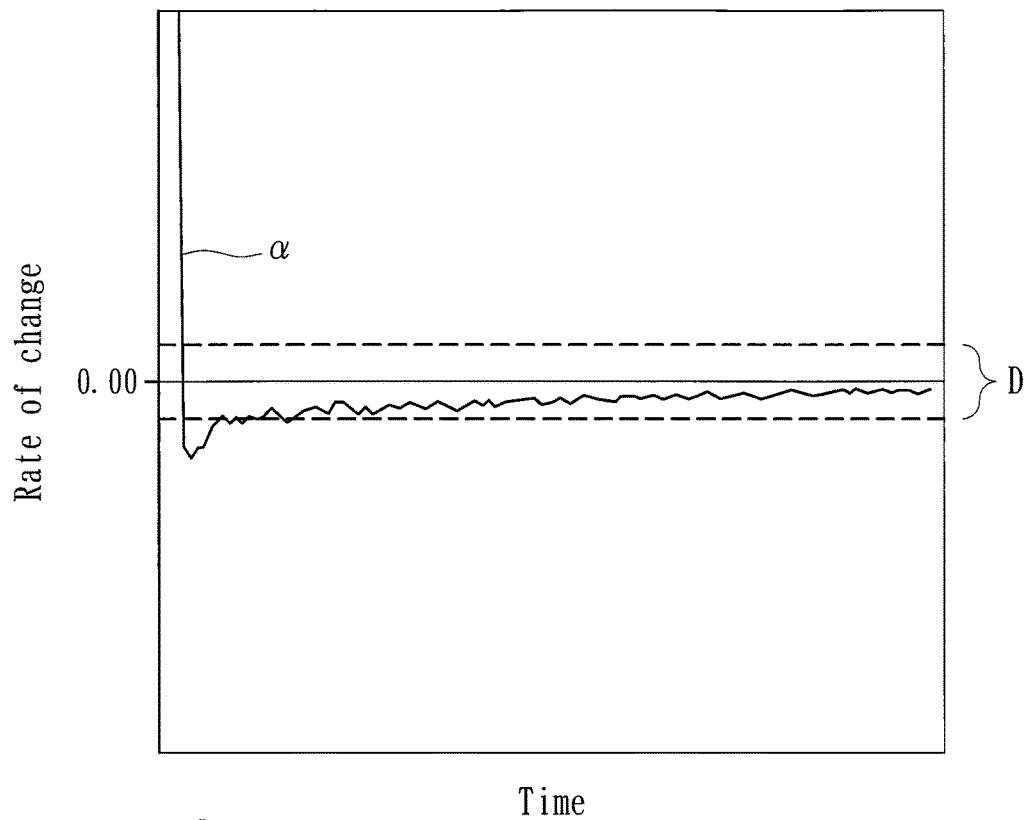
[Fig. 22]
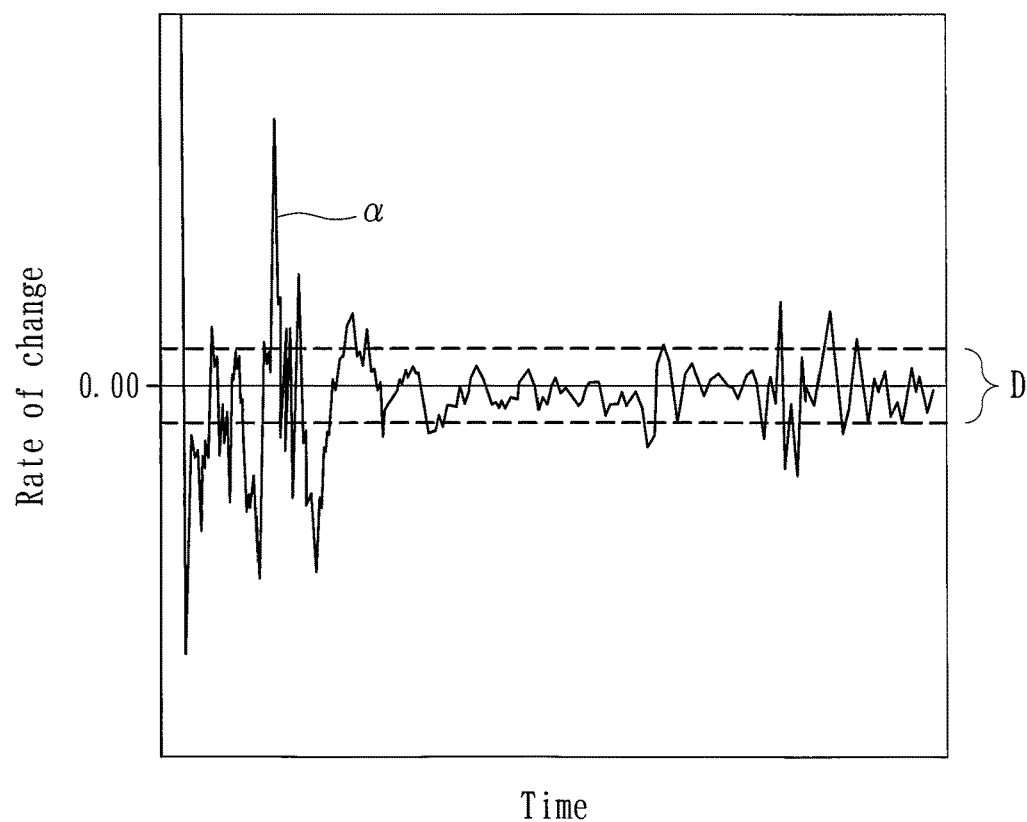

[Fig. 23]
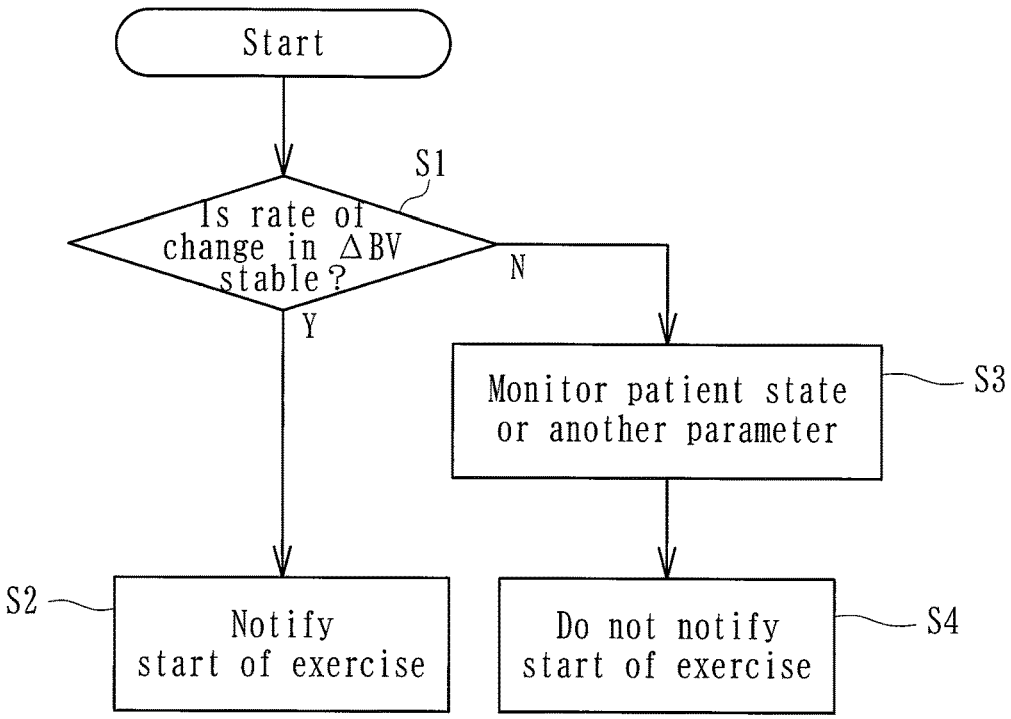
[Fig. 24]
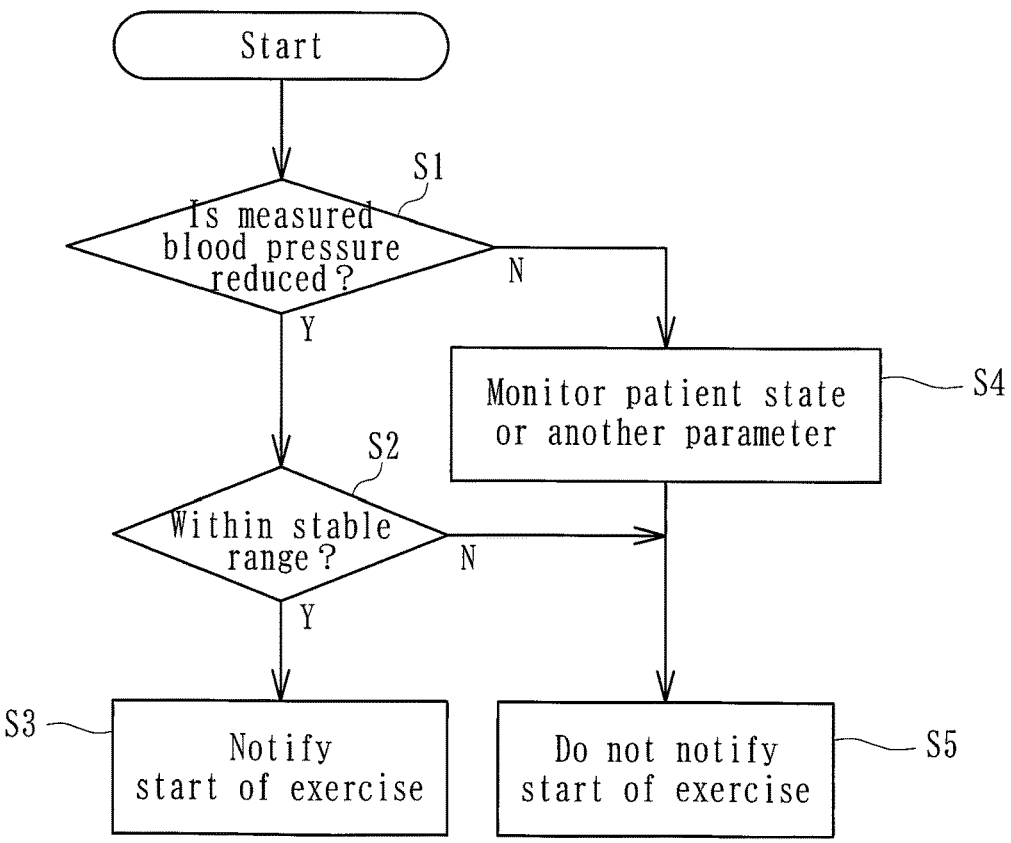

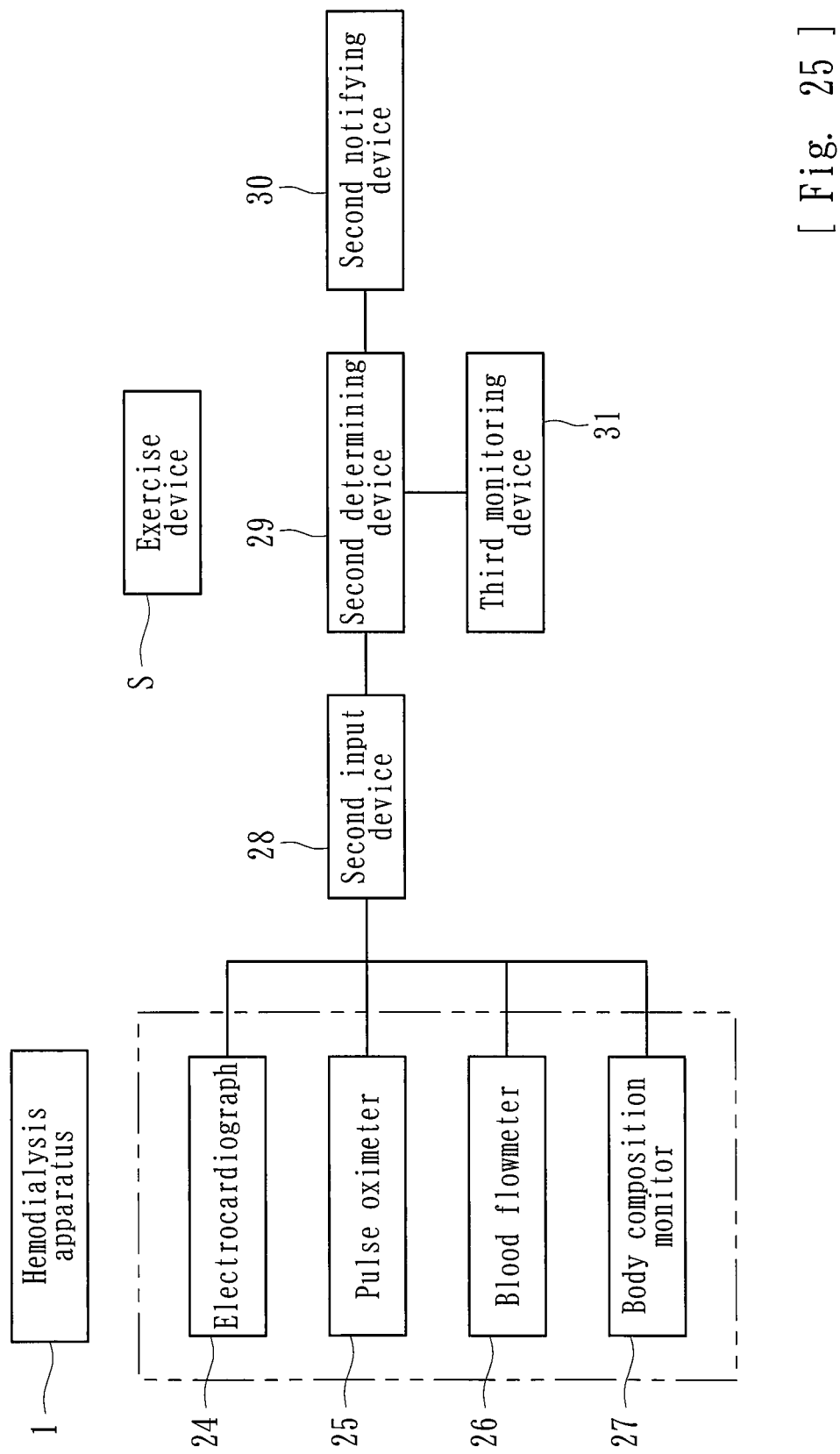
[Fig. 25]

[ Fig. 26 ]
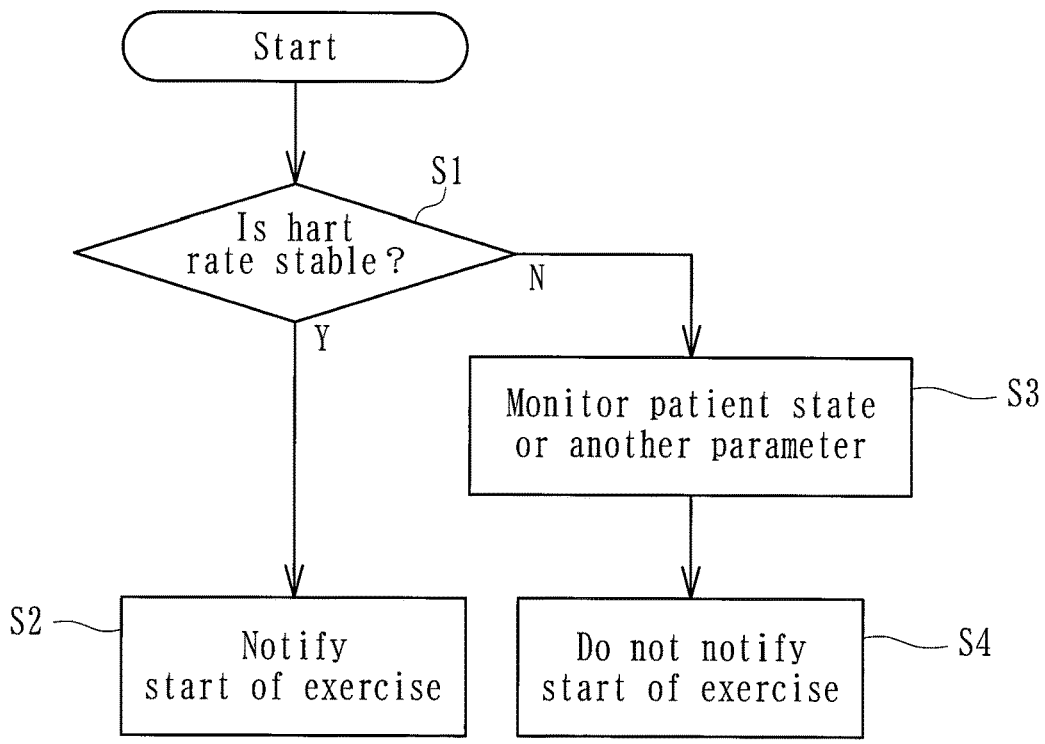
[ Fig. 27 ]
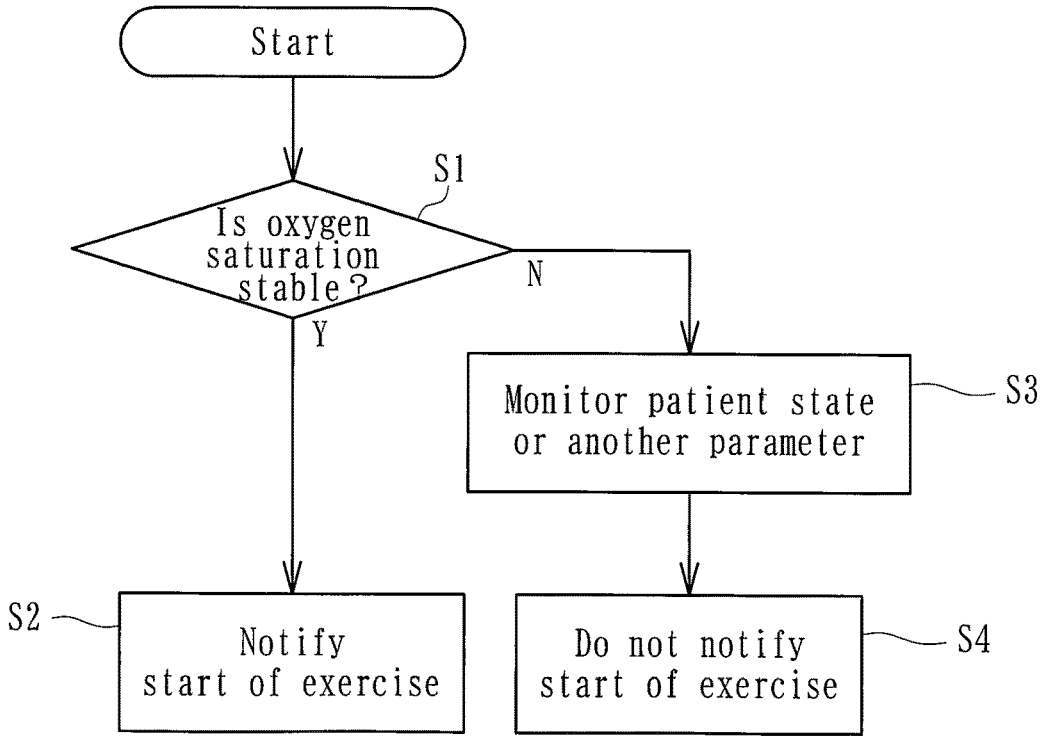

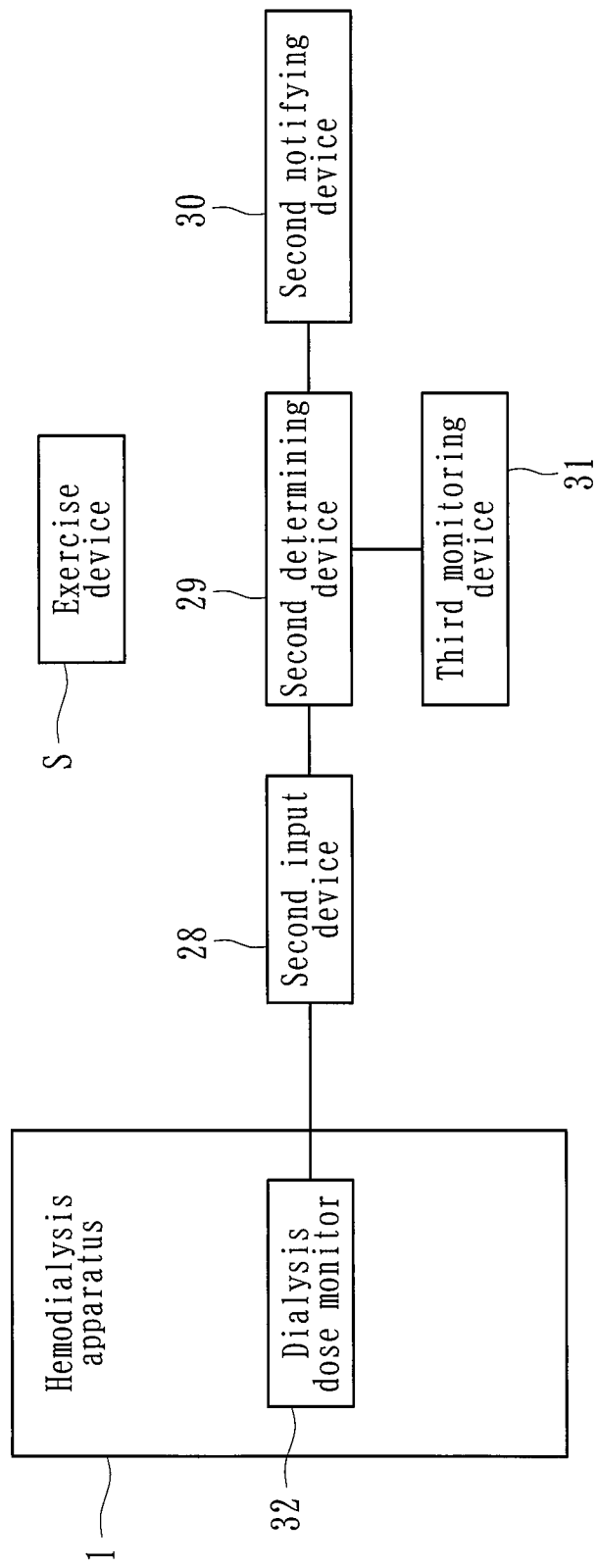
[ Fig. 28 ]

[Fig. 29]
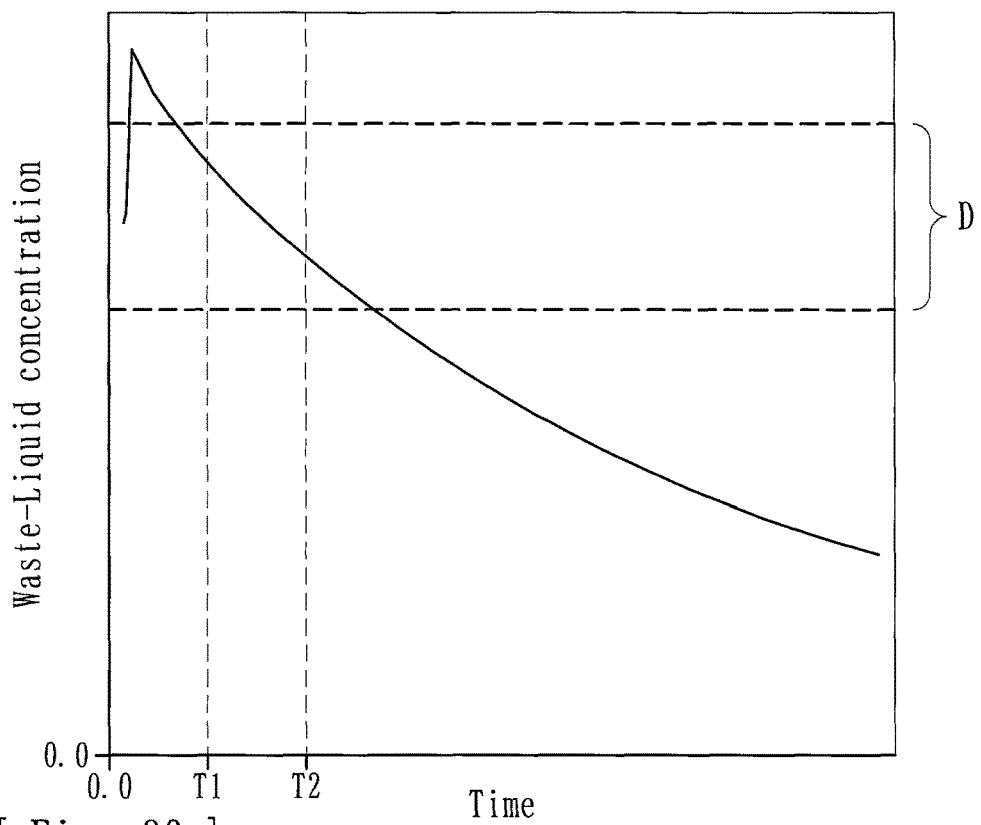
[Fig. 30]
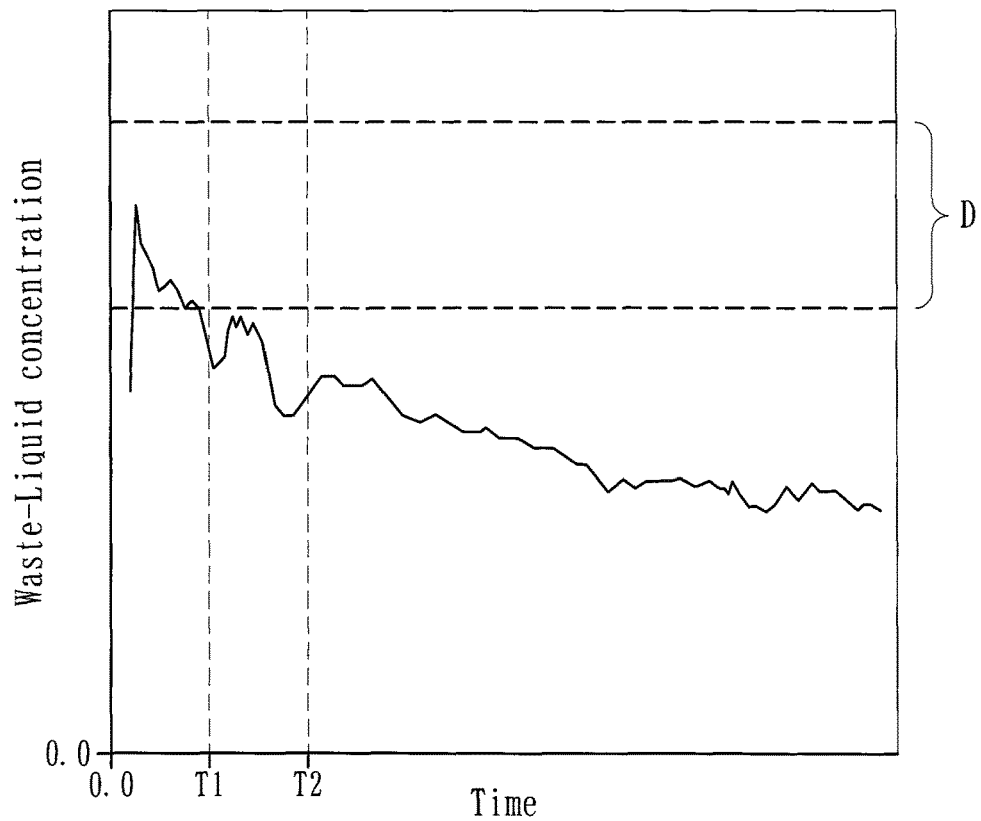

EXERCISE SUPPORT APPARATUS

FIELD

The present invention relates to an exercise support apparatus capable of supporting exercise taken by a patient during blood purification treatment.

BACKGROUND

In some recent-year cases, a patient who is taking blood purification treatment (for example, hemodialysis treatment) is made to take exercise. Exercise taken during blood purification treatment is expected to produce an effect of improving dialysis efficiency. During hemodialysis treatment, blood of the patient is in extracorporeal circulation. Hence, the number of kinds of exercise that can be taken is limited. Major examples of such exercise include aerobic exercise using a lower-limb ergometer fixed to a bed, aerobic exercise using a foot pedal fixed to a bed, strength training for chiefly lower limbs using a TheraBand, strength training for chiefly lower limbs using a balance ball, and so forth. Such prior-art techniques are not disclosed by any publicly known inventions, and there is no prior-art document to be cited herein.

SUMMARY

The above prior-art techniques have the following problem.

Patients who take blood purification treatment have low exercise tolerance. Therefore, exercise intensity is set to a low or moderate level in view of safety. Moreover, exercise intensity needs to be set to a level at which the patient does not feel extremely hard. In hitherto techniques, however, the solution is no more than checking the state of the patient during the exercise by medical staff including doctors who are watching around. There is a demand for an exercise support apparatus that can offer exercise during blood purification treatment with increased safety.

The present invention has been conceived in view of the above circumstances and provides an exercise support apparatus that can offer safer exercise to be taken during blood purification treatment.

According to the teachings herein, there is provided an exercise support apparatus capable of supporting exercise taken by a patient during blood purification treatment. The apparatus includes an estimation-line-generating device that generates an estimation line representing a course of a parameter regarding changes in circulating blood volume of the patient that is estimated to be observed after the exercise is started, the estimation line being generated after the blood purification treatment is started and from a continuous measurement of the parameter regarding changes in circulating blood volume that is conducted before the exercise is started; a first calculating device that calculates a difference or ratio between a measured value of the parameter regarding changes in circulating blood volume of the patient that is acquired after the exercise during the blood purification treatment is started and a value of the estimation line generated by the estimation-line-generating device; and a first monitoring device that monitors whether or not the difference or ratio calculated by the first calculating device is over a predetermined threshold.

According to the teachings herein, in the exercise support apparatus taught herein, if the difference or ratio calculated by the first calculating device is judged by the first monitoring device to be over the predetermined threshold, the exercise is stopped or information for stopping the exercise is provided.

According to the teachings herein, the exercise support apparatus according to the teachings herein further includes a comparing device that compares a tendency of changes in the difference or ratio calculated by the first calculating device during or after the exercise and an ideal tendency of changes in the difference or ratio; and a first judging device capable of judging whether or not the exercise taken during the blood purification treatment is appropriate from the comparison made by the comparing device.

According to the teachings herein, in the exercise support apparatus taught herein, the first judging device is capable of initiating a measurement of blood pressure of the patient or providing information that urges the measurement of blood pressure in accordance with the comparison made by the comparing device.

According to the teachings herein, in the exercise support apparatus taught herein, the parameter regarding changes in circulating blood volume of the patient is circulating-blood-volume rate of change that is measurable continuously during the blood purification treatment.

According to the teachings herein, in the exercise support apparatus taught herein, the parameter regarding changes in circulating blood volume of the patient is plasma refilling rate that is measurable continuously during the blood purification treatment.

According to the teachings herein, in the exercise support apparatus taught herein, the parameter regarding changes in circulating blood volume of the patient is detected by a sensor included in a blood purification apparatus intended for blood purification treatment.

According to the teachings herein, the exercise support apparatus taught herein, further includes a storage device that stores the parameter regarding changes in circulating blood volume of a particular patient or a parameter regarding a vital sign of the particular patient that is acquired while the exercise is taken during the blood purification treatment, perceived exertion experienced by the patient during the exercise, and an amount of exercise; a first determining device that determines an appropriate amount of exercise for the particular patient from the parameter, the amount of exercise, and the perceived exertion experienced by the patient that are stored in the storage device; and a first notifying device that notifies the appropriate amount of exercise for the particular patient that is determined by the first determining device.

According to the teachings herein, the exercise support apparatus taught herein further includes a second calculating device that calculates a difference or ratio between the parameter regarding changes in circulating blood volume or the parameter regarding the vital sign of the particular patient that is measured while the exercise is taken during a current blood purification treatment and the parameter regarding changes in circulating blood volume or the parameter regarding the vital sign that is stored in the storage device; and a second monitoring device that monitors whether or not the difference or ratio calculated by the second calculating device is over a predetermined threshold.

According to the teachings herein, in the exercise support apparatus taught herein, if the difference or ratio calculated by the second calculating device is judged by the second monitoring device to be over the predetermined threshold, a notification for a change in the amount of exercise is provided.

According to the teachings herein, in the exercise support apparatus taught herein, the parameter regarding changes in circulating blood volume of the patient is circulating-blood-volume rate of change that is measurable continuously during the blood purification treatment.

According to the teachings herein, in the exercise support apparatus taught herein, the parameter regarding changes in circulating blood volume of the patient is plasma refilling rate that is measurable continuously during the blood purification treatment.

According to the taught herein, in the exercise support apparatus taught herein, the parameter to be stored in the storage device is detected by a sensor included in a blood purification apparatus intended for blood purification treatment.

According to the teachings herein, the exercise support apparatus taught herein further includes a detection device for detecting the parameter regarding the vital sign of the patient.

According to the teachings herein, the exercise support apparatus taught herein further includes a second notifying device capable of notifying a timing of starting the exercise for each session of the blood purification treatment in accordance with a state of the patient or a state of the treatment.

According to the teachings herein, the exercise support apparatus taught herein further includes a second input device to which a parameter indicating circulatory dynamics of the patient that is acquired after the blood purification treatment is started is inputtable; and a second determining device that determines that the parameter inputted to the second input device is stabilized. The second notifying device is capable of notifying the timing of starting the exercise in accordance with the determination made by the second determining device.

According to the teachings herein, in the exercise support apparatus taught herein, if the parameter inputted to the second input device or a rate of change in the parameter follows a course that is continuously within a predetermined range, the parameter is determined by the second determining device to be stabilized, and the second notifying device is allowed to notify the timing of starting the exercise.

According to the teachings herein, in the exercise support apparatus taught herein, the parameter to be inputted to the second input device is the parameter regarding changes in circulating blood volume of the patient, the parameter regarding the vital sign of the patient, or a parameter regarding the blood purification treatment.

According to the teachings herein, in the exercise support apparatus taught herein, the parameter to be inputted to the second input device is detected by a sensor included in a blood purification apparatus intended for blood purification treatment.

According to the teachings herein, the exercise support apparatus taught herein further includes a detection device for detecting the parameter regarding the vital sign of the patient.

According to the teachings herein, the exercise support apparatus includes the estimation-line-generating device that generates an estimation line representing the course of the parameter regarding changes in circulating blood volume of the patient that is estimated to be observed after the exercise is started, the estimation line being generated after the blood purification treatment is started and from a continuous measurement of the parameter regarding changes in circulating blood volume that is conducted before the exercise is started; the first calculating device that calculates the difference or ratio between the measured value of the parameter regarding changes in circulating blood volume of the patient that is acquired after the exercise during the blood purification treatment is started and the value of the estimation line generated by the estimation-line-generating device; and the first monitoring device that monitors whether or not the difference or ratio calculated by the first calculating device is over the predetermined threshold. Therefore, safer exercise to be taken during blood purification treatment can be offered.

According to the teachings herein, if the difference or ratio calculated by the first calculating device is judged by the first monitoring device to be over the predetermined threshold, the exercise is stopped or information for stopping the exercise is provided. Therefore, the exercise can be stopped assuredly in accordance with the information, and the safety can be increased.

According to the teachings herein, the exercise support apparatus further includes the comparing device that compares the tendency of changes in the difference or ratio calculated by the first calculating device during or after the exercise and the ideal tendency of changes in the difference or ratio, and the first judging device capable of judging whether or not the exercise taken during the blood purification treatment is appropriate from the comparison made by the comparing device. Therefore, safe and appropriate exercise can be offered.

According to the teachings herein, the first judging device is capable of initiating the measurement of blood pressure of the patient or providing the information that urges the measurement of blood pressure in accordance with the comparison made by the comparing device. Therefore, the safety of the exercise can be provided with the measurement of blood pressure as well.

According to the teachings herein, the parameter regarding changes in circulating blood volume of the patient is the circulating-blood-volume rate of change that is measurable continuously during the blood purification treatment. Therefore, the first monitoring device can perform monitoring in accordance with the circulating-blood-volume rate of change that is detectable in real time.

According to the teachings herein, the parameter regarding changes in circulating blood volume of the patient is the plasma refilling rate that is measurable continuously during the blood purification treatment. Therefore, the first monitoring device can perform monitoring in accordance with the plasma refilling rate that is detectable in real time.

According to the teachings herein, the parameter regarding changes in circulating blood volume of the patient is detected by the sensor included in the blood purification apparatus intended for blood purification treatment. Therefore, the first monitoring device can perform monitoring by using the sensor intended for treatment.

According to the teachings herein, the exercise support apparatus further includes the storage device that stores the parameter regarding changes in circulating blood volume of a particular patient or the parameter regarding the vital sign of the particular patient that is acquired while the exercise is taken during the blood purification treatment, the perceived exertion experienced by the patient during the exercise, and the amount of exercise; the first determining device that determines the appropriate amount of exercise for the particular patient from the parameter, the amount of exercise, and the perceived exertion experienced by the patient that are stored in the storage device; and the first notifying device that notifies the appropriate amount of exercise for the particular patient that is determined by the first determining device. Therefore, exercise that is safer and more suitable for the particular patient can be offered during blood purification treatment.

According to the teachings herein, the exercise support apparatus further includes the second calculating device that calculates the difference or ratio between the parameter regarding changes in circulating blood volume or the parameter regarding the vital sign of the particular patient that is measured while the exercise is taken during the current blood purification treatment and the parameter regarding changes in circulating blood volume or the parameter regarding the vital sign that is stored in the storage device; and the second monitoring device that monitors whether or not the difference or ratio calculated by the second calculating device is over the predetermined threshold. Therefore, the safety during exercise can further be increased.

According to the teachings herein, if the difference or ratio calculated by the second calculating device is judged by the second monitoring device to be over the predetermined threshold, the notification for a change in the amount of exercise is provided. Therefore, the notification helps assuredly grasp the change in the amount of exercise, and the safety can be increased.

According to the teachings herein, the parameter regarding changes in circulating blood volume of the patient is the circulating-blood-volume rate of change that is measurable continuously during the blood purification treatment. Therefore, the monitoring by the second monitoring device can be performed in accordance with the circulating-blood-volume rate of change that is detectable in real time.

According to the teachings herein, the parameter regarding changes in circulating blood volume of the patient is the plasma refilling rate that is measurable continuously during the blood purification treatment. Therefore, the monitoring by the second monitoring device can be performed in accordance with the plasma refilling rate that is detectable in real time.

According to the teachings herein, the parameter to be stored in the storage device is detected by the sensor included in the blood purification apparatus intended for blood purification treatment. Therefore, the storing by the storage device can be performed by using the sensor intended for treatment.

According to the teachings herein, the exercise support apparatus further includes the detection device for detecting the parameter regarding the vital sign of the patient. Therefore, the appropriate amount of exercise for the particular patient that is determined by the first determining device can be grasped more accurately.

According to the teachings herein, the exercise support apparatus further includes the second notifying device capable of notifying the timing of starting the exercise for each session of the blood purification treatment in accordance with the state of the patient or the state of the treatment. Therefore, the exercise during the blood purification treatment can be started at an appropriate timing in accordance with the state of the patient or the state of the treatment.

According to the teachings herein, the exercise support apparatus further includes the second input device to which the parameter indicating circulatory dynamics of the patient that is acquired after the blood purification treatment is started is inputtable; and the second determining device that determines that the parameter inputted to the second input device is stabilized. The second notifying device is capable of notifying the timing of starting the exercise in accordance with the determination made by the second determining device. Therefore, the exercise can be started at a more appropriate timing.

According to the teachings herein, if the parameter inputted to the second input device or the rate of change in the parameter follows the course that is continuously within the predetermined range, the parameter is determined by the second determining device to be stabilized, and the second notifying device is allowed to notify the timing of starting the exercise. Therefore, the timing of starting the exercise can be notified accurately.

According to the teachings herein, the parameter to be inputted to the second input device is the parameter regarding changes in circulating blood volume of the patient, the parameter regarding the vital sign of the patient, or the parameter regarding the blood purification treatment. Therefore, the timing of starting the exercise can be notified more accurately.

According to the teachings herein, the parameter to be inputted to the second input device is detected by the sensor included in the blood purification apparatus intended for blood purification treatment. Therefore, the timing of starting the exercise can be notified by using the sensor intended for treatment.

According to the teachings herein, the exercise support apparatus further includes the detection device for detecting the parameter regarding the vital sign of the patient. Therefore, when the timing of starting the exercise is notified, the state of the patient can be grasped more accurately.

BRIEF DESCRIPTION OF THE DRAWINGS

FIG. 1 is a block diagram illustrating an exercise support apparatus according to an embodiment of the present invention.

FIG. 2 is a schematic diagram illustrating an outline of a hemodialysis apparatus applicable to the exercise support apparatus.

FIG. 3 is a schematic diagram illustrating a configuration of an apparatus body of the blood purification apparatus.

FIG. 4 is a graph illustrating an estimation line generated by the exercise support apparatus.

FIG. 5 includes graphs illustrating courses of $\Delta BV$ and deviations in $\Delta BV$ from the estimation line.

FIG. 6 is a flow chart illustrating a control process performed by the exercise support apparatus.

FIG. 7 is a flow chart illustrating another control process performed by the exercise support apparatus.

FIG. 8 is a graph illustrating the difference between $\Delta BV$ after blood purification treatment and the estimation line.

FIG. 9 includes graphs illustrating an estimation line generated by an exercise support apparatus according to another embodiment of the present invention, courses of PRR, and deviations in PRR from the estimation line.

FIG. 10 is a block diagram illustrating an exercise support apparatus according to a second embodiment of the present invention.

FIG. 11 is a graph illustrating courses of circulating-blood-volume rate of change acquired for a particular patient during exercise.

FIG. 12 includes tables of the Borg scale and the modified Borg scale used in the exercise support apparatus.

FIG. 13 is a graph for comparison between past courses of circulating-blood-volume rate of change ($\Delta BV$) and the current course of the same that are acquired for a particular patient by the exercise support apparatus.

FIG. 14 is a graph for comparison between past courses of a vital sign (blood pressure) and the current course of the same that are acquired for a particular patient by the exercise support apparatus.

FIG. 15 is a graph for comparison between past courses of plasma refilling rate (PRR) and the current course of the same that are acquired for a particular patient by the exercise support apparatus.

FIG. 16 is a block diagram illustrating an exercise support apparatus according to a third embodiment of the present invention.

FIG. 17 is a graph for comparison between past courses of a vital sign (cardiac output) and the current course of the same that are acquired for a particular patient by the exercise support apparatus.

FIG. 18 is a graph for comparison between past courses of another vital sign (heart rate) and the current course of the same that are acquired for a particular patient by the exercise support apparatus.

FIG. 19 is a graph for comparison between past courses of yet another vital sign (oxygen uptake) and the current course of the same that are acquired for a particular patient by the exercise support apparatus.

FIG. 20 is a block diagram illustrating an exercise support apparatus according to a fourth embodiment of the present invention.

FIG. 21 is a graph illustrating a course of circulating-blood-volume rate of change of a patient that is determined to be stable.

FIG. 22 is a graph illustrating a course of circulating-blood-volume rate of change of a patient that is not determined to be stable.

FIG. 23 is a flow chart illustrating a control process performed by the exercise support apparatus.

FIG. 24 is a flow chart illustrating another control process performed by the exercise support apparatus.

FIG. 25 is a block diagram illustrating an exercise support apparatus according to a fifth embodiment of the present invention.

FIG. 26 is a flow chart illustrating a control process performed by the exercise support apparatus.

FIG. 27 is a flow chart illustrating another control process performed by the exercise support apparatus.

FIG. 28 is a block diagram illustrating an exercise support apparatus according to a sixth embodiment of the present invention.

FIG. 29 is a graph of waste-liquid concentration that is determined to be stable.

FIG. 30 is a graph of waste-liquid concentration that is not determined to be stable.

DETAILED DESCRIPTION

Embodiments of the present invention will now be described specifically with reference to the drawings.

An exercise support apparatus according to a first embodiment is capable of supporting exercise taken by a patient during blood purification treatment and includes, as illustrated in FIG. 1, a blood volume meter 2 and a blood pressure monitor 3 that are included in a hemodialysis apparatus 1 intended for blood purification treatment (dialysis treatment), an exercise device S, an estimation-line-generating device 4, a first calculating device 5, a first monitoring device 6, an informing device 7, a comparing device 8, and a first judging device 9.

As illustrated in FIGS. 2 and 3, the hemodialysis apparatus 1 applicable to the present embodiment basically includes a blood circuit 10 for causing blood of the patient to extracorporeally circulate therethrough, a dialyzer 11 connected to the blood circuit 10 and provided for hemodialysis, and a dialysis-apparatus body 14 connected to the dialyzer 11 and that supplies and ultrafilters dialysate. As illustrated in the drawings, the blood circuit 10 basically includes an arterial blood circuit 10a and a venous blood circuit 10b each formed of a flexible tube. The dialyzer 11 is provided between the arterial blood circuit 10a and the venous blood circuit 10b.

The arterial blood circuit 10a is provided with an arterial puncture needle a at a distal end thereof and with a peristaltic blood pump 12 and a hematocrit sensor 17 at respective halfway positions thereof. The venous blood circuit 10b is provided with a venous puncture needle b at a distal end thereof and with an air trap chamber 13 for bubble removal at a halfway position thereof. In this specification, the side on which the puncture needle for blood removal (blood collection) is provided is referred to as the "arterial" side, and the side on which the puncture needle for blood return is provided is referred to as the "venous" side. The "arterial" side and the "venous" side are not defined on the basis of which of the artery and the vein is to be the object of puncture.

When the blood pump 12 is activated with the arterial puncture needle a and the venous puncture needle b being stuck in the patient, blood of the patient flows into the arterial blood circuit 10a and reaches the dialyzer 11, where the blood is purified. Then, the blood flows through the venous blood circuit 10b while being subjected to bubble removal in the air trap chamber 13, and is returned into the body of the patient. Thus, the blood of the patient is purified by the dialyzer 11 while being caused to extracorporeally circulate through the blood circuit 10.

The dialyzer 11 has, in a housing thereof, a blood introduction port 11a, a blood delivery port 11b, a dialysate introduction port 11c, and a dialysate delivery port 11d. The blood introduction port 11a receives a proximal end of the arterial blood circuit 10a connected thereto. The blood delivery port 11b receives a proximal end of the venous blood circuit 10b connected thereto. The dialysate introduction port 11c and the dialysate delivery port 11d receive a dialysate introduction line L1 and a dialysate drain line L2, respectively, connected thereto. The dialysate introduction line L1 and the dialysate drain line L2 each extend from the dialysis-apparatus body 14.

The dialyzer 11 includes a plurality of hollow fibers. The inside of each of the hollow fibers forms a blood flow route, and a space between the inner peripheral surface of the housing and the outer peripheral surfaces of the hollow fibers forms a dialysate flow route. Each hollow fiber has a number of very small holes (pores) extending therethrough from the outer peripheral surface to the inner peripheral surface and thus forms a hollow fiber membrane. Impurities and the like contained in the blood are allowed to penetrate through the membranes into the dialysate.

On the other hand, as illustrated in FIG. 3, the dialysis-apparatus body 14 basically includes a duplex pump P provided over the dialysate introduction line L1 and the dialysate drain line L2, a bypass line L3 connected to the dialysate drain line L2 in such a manner as to bypass the duplex pump P, and an ultrafiltration pump 16 connected to the bypass line L3. When the duplex pump P is activated, dialysate supplied from a dialysate supply device 15 flows into the dialysate introduction line L1 and reaches the dialyzer 11. Then, the dialysate flows into the dialysate drain line L2 and into the bypass line L3, and is drained to the outside of the apparatus.

The ultrafiltration pump 16 is provided for performing ultrafiltration in which water is removed from the blood of the patient flowing through the dialyzer 11. When the ultrafiltration pump 16 is activated, the amount of liquid drained through the dialysate drain line L2 becomes greater than the amount of dialysate introduced through the dialysate introduction line L1. Hence, water is removed from the blood by an amount corresponding to the excess. The duplex pump P may be replaced with another device of a so-called balancing-chamber type.

The hematocrit sensor 17 is capable of detecting, in the time course of dialysis treatment, the concentration of the blood (blood concentration) extracorporeally circulating through the blood circuit 10. The hematocrit sensor 17 includes, for example, a light-emitting element such as an LED and a light-receiving element such as a photodiode. The light-emitting element applies light at a predetermined wavelength to the blood, and the light transmitted through or reflected by the blood is received by the light-receiving element, whereby the hematocrit value indicating the concentration of the blood of the patient that is in extracorporeal circulation through the blood circuit 10 is measured. The hematocrit value is a benchmark for blood concentration and is specifically expressed as the ratio of the volume of red blood cells to the total volume of blood.

The dialysis-apparatus body 14 includes the blood volume meter 2 as a sensor capable of detecting circulating-blood-volume rate of change ($\Delta BV$), and the blood pressure monitor 3 as a sensor capable of detecting the blood pressure of the patient. The blood volume meter 2 is electrically connected to the hematocrit sensor 17 and is capable of detecting the circulating-blood-volume rate of change ($\Delta BV$) from the hematocrit value (blood concentration) transmitted thereto from the hematocrit sensor 17. Specifically, letting the hematocrit value acquired by the hematocrit sensor 17 be Ht, the circulating-blood-volume rate of change $\Delta BV$ can be calculated in accordance with the following arithmetic expression: (Ht at the start of dialysis−Measured Ht)/Measured Ht×100. Thus, the circulating-blood-volume rate of change ($\Delta BV$) of the patient can be detected in real time in the time course of dialysis treatment.

In the present embodiment, the circulating-blood-volume rate of change ($\Delta BV$) is calculated from the measured hematocrit value. Alternatively, the circulating-blood-volume rate of change ($\Delta BV$) may be calculated from, for example, hemoglobin concentration, the total protein concentration of serum, or the like. To measure a parameter for calculating the circulating-blood-volume rate of change ($\Delta BV$), any kind of instrument may be used, such as an optical instrument or an ultrasonic instrument.

The exercise device S is a device for the patient to do exercise during blood purification treatment (dialysis treatment, in the present embodiment). The exercise device S is, for example, a lower-limb ergometer fixed to a bed, a foot pedal fixed to a bed, a TheraBand or a balance ball for strength training, or the like. There is no need to prepare a specific piece of equipment or the like, as long as the patient can take exercise, such as stretching or gymnastic exercise, during blood purification treatment (dialysis treatment, in the present embodiment).

The exercise support apparatus according to the present embodiment includes the estimation-line-generating device 4 electrically connected to the blood volume meter 2, the first calculating device 5, the first monitoring device 6, the informing device 7, the comparing device 8, and the first judging device 9 electrically connected to the blood pressure monitor 3 and to the informing device 7. The estimation-line-generating device 4 generates an estimation line representing a course of the circulating-blood-volume rate of change ($\Delta BV$) (a parameter regarding changes in circulating blood volume) of the patient that is estimated to be observed after the exercise is started. The estimation line is generated after the blood purification treatment (dialysis treatment) is started and from a continuous measurement of the circulating-blood-volume rate of change ($\Delta BV$) (the parameter regarding changes in circulating blood volume) that is conducted before the exercise is started.

For example, as illustrated in FIG. 4, a value $\beta 0$ of the circulating-blood-volume rate of change of a patient is measured by the blood volume meter 2 continuously from the start of the blood purification treatment until exercise start time T1. On the basis of the circulating-blood-volume rate of change $\beta 0$ of the patient that is measured continuously before the exercise is started, an estimation line $\alpha$ can be generated as a course of the circulating-blood-volume rate of change ($\Delta BV$) that is estimated to be observed after the exercise is started. The estimation line $\alpha$ according to the present embodiment is an approximate straight line. Alternatively, the estimation line $\alpha$ may be an approximate curve.

After the blood purification treatment is started, as illustrated in FIG. 5, exercise using the exercise device S or the like is taken from the exercise start time T1 to exercise end time T2. Accordingly, the circulating-blood-volume rate of change ($\Delta BV$) measured by the blood volume meter 2 changes with time (for example, the course of the circulating-blood-volume rate of change ($\Delta BV$) to be observed after the start of the exercise is estimated to form any of a pattern $\beta 1$, a pattern $\beta 2$, and a pattern ($\beta 3$). As illustrated in the upper graph in FIG. 5, the measurement of the circulating-blood-volume rate of change ($\Delta BV$) by the blood volume meter 2 is continued even after the exercise end time T2.

The first calculating device 5 is provided for calculating the difference (or ratio) between the measured value of the circulating-blood-volume rate of change ($\Delta BV$) (the parameter regarding changes in circulating blood volume) of the patient that is acquired after the exercise during the blood purification treatment is started and the value of the estimation line $\alpha$ generated by the estimation-line-generating device 4. The difference calculated by the first calculating device 5 is plotted as follows. For example, defining a case of no difference (no deviation) from the estimation line $\alpha$ as zero, a positive difference is plotted in a zone above zero, and a negative difference is plotted in a zone below zero. Consequently, as illustrated in the lower graph in FIG. 5, a pattern $\gamma 1$ corresponding to the pattern $\beta 1$, a pattern $\gamma 2$ corresponding to the pattern $\beta 2$, and a pattern $\gamma 3$ corresponding to the pattern $\beta 3$ are obtained. As can be seen from the graph in the drawing, the first calculating device 5 is capable of calculating the difference (or ratio) even after the exercise end time T2.

The first monitoring device 6 monitors whether or not the difference (or ratio) calculated by the first calculating device 5 is over a predetermined threshold. For example, letting the predetermined threshold be d as denoted in the lower graph in FIG. 5, the pattern $\gamma 3$ goes over the threshold d at a point during the exercise. At that point of time, the difference is judged by the first monitoring device 6 to be over the threshold d. In such a case, there may be a worsening of the patient's condition. Therefore, the exercise needs to be stopped (aborted) immediately.

The informing device 7 provides information for stopping the exercise if the difference (or ratio) calculated by the first calculating device 5 is judged by the first monitoring device 6 to be over the predetermined threshold d. The informing device 7 may be, for example, a device that indicates the stoppage of the exercise on a monitor, a device that generates a warning with a sound effect or a voice sound, a device that turns on a warning lamp or causes a warning lamp to blink, or the like. Alternatively, the informing device 7 may be any of a device that uses an element included in the hemodialysis apparatus 1, a dedicated device, and the like. As an alternative to or in addition to providing information as described above, the informing device 7 may stop the exercise. For example, the informing device 7 may forcibly stop the exercise device S.

The comparing device 8 is provided for comparing the tendency of changes in the difference or ratio (the deviation between the circulating-blood-volume rate of change ($\Delta BV$) measured by the blood volume meter 2 and the value of the estimation line $\alpha$) calculated by the first calculating device 5 during or after the exercise and an ideal tendency of changes in the difference or ratio. After the exercise is finished, refilling is promoted. Therefore, the circulating-blood-volume rate of change ($\Delta BV$) normally increases. Accordingly, in the ideal tendency of changes, the difference calculated by the first calculating device 5 is negative (the value of the estimation line $\alpha$ is greater than the circulating-blood-volume rate of change ($\Delta BV$) measured by the blood volume meter 2) during a period from the start of the exercise until the end of the exercise, whereas the differences calculated by the first calculating device 5 is positive (the value of the estimation line $\alpha$ is smaller than the circulating-blood-volume rate of change ($\Delta BV$) measured by the blood volume meter 2) after the end of the exercise.

The first judging device 9 is capable of judging whether or not the exercise taken during the blood purification treatment is appropriate from the comparison made by the comparing device 8. Regarding the tendencies of changes compared by the comparing device 8, if the tendency of changes in the difference or ratio calculated by the first calculating device 5 is judged to be approximate to the ideal tendency of changes in the difference or ratio, the exercise can be judged to be appropriate. However, if the tendency of changes in the difference or ratio calculated by the first calculating device 5 forms, for example, the pattern $\gamma 1$ illustrated in the lower graph in FIG. 5, the amount of exercise is judged to be insufficient, because the circulating-blood-volume rate of change ($\Delta BV$) does not become lower than the ideal tendency of changes even after the exercise is started. If such a result is not improved even after a long-term treatment, the dry weight of the patient is to be reviewed, preferably.

If the tendency of changes in the difference or ratio calculated by the first calculating device 5 forms, for example, the pattern $\gamma 2$ illustrated in the lower graph in FIG. 5, there may be an insufficiency of refilling, because the circulating-blood-volume rate of change ($\Delta BV$) does not recover to the ideal tendency of changes even after the exercise is finished. Such a case may trigger a drop of blood pressure. Therefore, the blood pressure of the patient is measured, or information that urges the measurement of blood pressure is provided. If the tendency of changes in the difference or ratio calculated by the first calculating device 5 forms the pattern $\gamma 3$, the exercise is stopped immediately, as described above.

Now, a control process according to the present embodiment will be described with reference to the flow charts illustrated in FIGS. 6 and 7.

When a predetermined period of time elapses after the treatment is started, the estimation-line-generating device 4 generates an estimation line $\alpha$ in step S1. Then, in step S2, the calculation by the first calculating device 5 and the monitoring by the first monitoring device 6 are performed until the exercise is finished. In step S2, if the result of the calculation (the difference or ratio calculated) by the first calculating device 5 is determined to be small (for example, below 1%), the process proceeds to step S3, where the result is judged by the first monitoring device 6 to be normal. In contrast, if the result of the calculation (the difference or ratio calculated) by the first calculating device 5 is determined to be large (for example, over 2%, i.e., over the predetermined threshold d), the process proceeds to step S5, where the informing device 7 provides corresponding information.

In step S2, if the result of the calculation (the difference or ratio calculated) by the first calculating device 5 is determined to be moderate (for example, 1% to 2%), the process proceeds to step S4, where information that the blood pressure is to be measured is provided. If the result of the measurement of blood pressure falls within a normal range, the result is determined to be normal in step S3. If the result of the measurement of blood pressure is out of the normal range, the informing device 7 provides corresponding information in step S5. Then, as illustrated in FIG. 7, if ten minutes elapses (in step S6) after the exercise is finished, the calculation by the first calculating device 5 and the monitoring by the first monitoring device 6 are performed in step S7 until the exercise is finished.

In step S7, if the result of the calculation (the difference or ratio calculated) by the first calculating device 5 is determined to be small (for example, below 1%), the process proceeds to step S8, where the result is judged by the first monitoring device 6 to be normal. If the result of the calculation (the difference or ratio calculated) by the first calculating device 5 is determined to be large (for example, over 2%, i.e., over the predetermined threshold d), the process proceeds to step S10, where the informing device 7 provides corresponding information. In step S7, if the result of the calculation (the difference or ratio calculated) by the first calculating device 5 is determined to be moderate (for example, 1% to 2%), the process proceeds to step S9, where information that the blood pressure is to be measured is provided. If the result of the measurement of blood pressure falls within the normal range, the result is determined to be normal in step S8. If the result of the measurement of blood pressure is out of the normal range, the informing device 7 provides corresponding information in step S10.

The difference (or ratio) from the estimation line $\alpha$ of the circulating-blood-volume rate of change ($\Delta BV$) that is acquired after the dialysis treatment is recorded as illustrated in FIG. 8. If the difference (or ratio) is positive for a plurality of dialysis-treatment sessions (if there is a large deviation between the circulating-blood-volume rate of change ($\Delta BV$) measured by the blood volume meter 2 and the value of the estimation line $\alpha$), a change in the setting of the amount of exercise or the dry weight may be advised.

According to the above first embodiment, the exercise support apparatus includes the estimation-line-generating device 4 that generates an estimation line $\alpha$ representing a course of the parameter regarding changes in circulating blood volume of the patient that is estimated to be observed after the exercise is started, the estimation line $\alpha$ being generated after the blood purification treatment is started and from a continuous measurement of the parameter regarding changes in circulating blood volume (in the present embodiment, the circulating-blood-volume rate of change (ΔBV)) that is conducted before the exercise is started; the first calculating device 5 that calculates the difference or ratio between the measured value of the parameter regarding changes in circulating blood volume of the patient that is acquired after the exercise during the blood purification treatment is started and the value of the estimation line α generated by the estimation-line-generating device 4; and the first monitoring device 6 that monitors whether or not the difference or ratio calculated by the first calculating device 5 is over a predetermined threshold. Therefore, safer exercise to be taken during blood purification treatment can be offered.

In particular, if the difference or ratio calculated by the first calculating device 5 is judged by the first monitoring device 6 to be over the predetermined threshold d, the exercise is stopped or information for stopping the exercise is provided. Therefore, the exercise can be stopped assuredly in accordance with the information, and the safety can be increased. The exercise support apparatus further includes the comparing device 8 that compares the tendency of changes in the difference or ratio calculated by the first calculating device 5 during or after the exercise and an ideal tendency of changes in the difference or ratio, and the first judging device 9 capable of judging whether or not the exercise taken during the blood purification treatment is appropriate from the comparison made by the comparing device 8. Therefore, safe and appropriate exercise can be offered.

The first judging device 9 is capable of initiating the measurement of blood pressure of the patient or providing information that urges the measurement of blood pressure in accordance with the comparison made by the comparing device 8. Therefore, the safety of the exercise can be provided with the measurement of blood pressure as well. The parameter regarding changes in circulating blood volume of the patient is the circulating-blood-volume rate of change (ΔBV) that is measurable continuously during the blood purification treatment. Therefore, the first monitoring device 6 can perform monitoring in accordance with the circulating-blood-volume rate of change (ΔBV) that is detectable in real time. In particular, the parameter regarding changes in circulating blood volume (the circulating-blood-volume rate of change (ΔBV)) of the patient is detected by a sensor (the blood volume meter 2) included in the blood purification apparatus 1 intended for blood purification treatment. Therefore, the first monitoring device 6 can perform monitoring by using the sensor intended for treatment.

While the exercise support apparatus according to the first embodiment has been described above, the present invention is not limited thereto. For example, the parameter regarding changes in circulating blood volume of the patient may alternatively be plasma refilling rate (PRR) that is measurable continuously during the blood purification treatment. The plasma refilling rate (PRR) is calculable by using the blood volume meter 2 of the hemodialysis apparatus 1 and in accordance with the following arithmetic expression, assuming that the circulating blood volume of the patient is 1/13 of the body weight before the treatment.

PRR=(Ultrafiltration volume during measurement period+Increment in circulating blood volume during measurement period)/Duration of measurement period Increment in circulating blood volume during measurement period=Circulating blood volume×Rate of change in ΔBV during measurement period Circulating blood volume=Body weight before treatment/13

If the plasma refilling rate (PRR) is taken as the parameter regarding changes in circulating blood volume of the patient, an estimation line α illustrated in the upper graph in FIG. 9 can be generated by the estimation-line-generating device 4. Furthermore, when the difference or ratio between the measured value of the plasma refilling rate (PRR) of the patient that is acquired after the exercise during blood purification treatment is started and the value of the estimation line α generated by the estimation-line-generating device 4 is calculated by the first calculating device 5, the lower graph illustrated in FIG. 9 is obtained. In such a case, the monitoring by the first monitoring device 6, the comparison by the comparing device 8, and the judgement by the first judging device 9 are performed in the same manner as in the above embodiment. Furthermore, the first monitoring device 6 can perform monitoring in accordance with the plasma refilling rate that is detectable in real time.

In the present embodiment, the parameter regarding changes in circulating blood volume of the patient is the circulating-blood-volume rate of change (ΔBV) or the plasma refilling rate (PRR). Alternatively, another parameter may be taken. Furthermore, the parameter regarding changes in circulating blood volume of the patient is detected by a sensor included in the blood purification apparatus intended for blood purification treatment. Alternatively, the parameter may be detected by a sensor provided separately from the blood purification apparatus. Moreover, while the present embodiment concerns a case where the present invention is applied to the hemodialysis apparatus 1 intended for hemodialysis treatment, the present invention may alternatively be applied to a blood purification apparatus intended for another kind of blood purification treatment.

Now, a second embodiment of the present invention will be described.

An exercise support apparatus according to the second embodiment is capable of supporting exercise taken by a patient during blood purification treatment and includes, as illustrated in FIG. 10, a blood volume meter 2 and a blood pressure monitor 3 that are included in a hemodialysis apparatus 1 intended for blood purification treatment (dialysis treatment), an exercise device S, a first input device W, a storage device 18, a first determining device 19, a first notifying device 20, a second calculating device 21, a second monitoring device 22, and a second judging device 23. Elements that are the same as those described in the first embodiment are denoted by corresponding ones of the reference numerals, and detailed description of such elements is omitted.

The exercise support apparatus according to the present embodiment includes the storage device 18 electrically connected to the blood volume meter 2 and to the blood pressure monitor 3, the first determining device 19, the first notifying device 20, the second calculating device 21, the second monitoring device 22, and the second judging device 23. The storage device 18 stores the circulating-blood-volume rate of change (ΔBV) (the parameter regarding changes in circulating blood volume) of a particular patient or the blood pressure (a parameter regarding a vital sign) of the particular patient that is acquired while the exercise is taken during the blood purification treatment. The storage device 18 further stores the perceived exertion experienced by the patient during the exercise, and the amount of exercise.

For example, if the value of the circulating-blood-volume rate of change (ΔBV) (the parameter regarding changes in circulating blood volume) of the particular patient is measured continuously by the blood volume meter 2 during a period from the start of the blood purification treatment through a middle and the end of the exercise until the end of the blood purification treatment, the following can be acquired, as illustrated in FIG. 11: a course (a pattern α) of the circulating-blood-volume rate of change (ΔBV) in a case where the amount of exercise is appropriate (the intensity of exercise stress is appropriate), a course (a pattern β) of the circulating-blood-volume rate of change (ΔBV) in a case where the amount of exercise is excessive (the intensity of exercise stress is higher than appropriate), and a course (a pattern γ) of the circulating-blood-volume rate of change (ΔBV) in a case where the amount of exercise is insufficient (the intensity of exercise stress is lower than appropriate).

If the value of the blood pressure (the parameter regarding the vital sign) of the particular patient is measured continuously by the blood pressure monitor 3 during the period from the start of the blood purification treatment through a middle and the end of the exercise until the end of the blood purification treatment, courses of changes corresponding to different amounts of exercise (see α1 and α2 illustrated in FIG. 14) can be acquired. The storage device 18 according to the present embodiment stores courses of the circulating-blood-volume rate of change (ΔBV) (the parameter regarding changes in circulating blood volume) of the particular patient that are measured by the blood volume meter 2, and courses of the blood pressure (the parameter regarding the vital sign) of the particular patient that are measured by the blood pressure monitor 3.

The first input device W is provided for inputting the perceived exertion experienced by the patient during the exercise, and the amount of exercise. The input may be made by any of the following, for example: a keyboard (including a numeric keypad), a mouse, a touch sensor accepting input with a finger touching a given position of a screen, and the like. The amount of exercise indicates the intensity of exercise stress generated by the exercise device S. Preferably, for example, the amount of exercise is expressed in a numerical grade and is inputtable on the first input device W. The exercise device S and the storage device 18 may be electrically connected to each other, so that the intensity of exercise stress that is set on the exercise device S can be stored in the storage device 18, with no use of the first input device W.

The perceived exertion refers to the degree of hardness perceived by the patient during the exercise and may be expressed in accordance with the Borg scale or the modified Borg scale (indices used in exercise physiology) illustrated in FIG. 12. For example, hearing or the like is conducted to the patient who is taking the exercise, and the degree of hardness of the exercise is expressed by a numerical grade defined by the Borg scale or the modified Borg scale. The perceived exertion and the amount of exercise described above are inputted on the first input device W and are stored in the storage device 18 in association (link) with data regarding the course of the circulating-blood-volume rate of change (ΔBV) or data regarding the course of the blood pressure. Alternatively, the perceived exertion and the amount of exercise may be stored not in association (link) with the data regarding the course of the circulating-blood-volume rate of change (ΔBV) or the data regarding the course of the blood pressure.

The first determining device 19 determines an appropriate amount of exercise for the particular patient from the parameter, the amount of exercise, and the perceived exertion experienced by the patient that are stored in the storage device 18. For example, among such data regarding past courses stored in the storage device 18, those corresponding to "Somewhat hard" (13 in the Borg scale) or "Somewhat strong" (4 in the modified Borg scale) in the Borg scale or in the modified Borg scale are determined to be acquired with the appropriate amount of exercise for the particular patient.

The first notifying device 20 is provided for notifying the appropriate amount of exercise for the particular patient that is determined by the first determining device 19. The first notifying device 20 may be in any form such as a display that indicates the appropriate amount of exercise, an informing device that informs the appropriate amount of exercise with a voice sound, or the like. The amount of exercise notified by the first notifying device 20 may be taken as a reference for an exercise prescription to be made by medical staff such as a doctor. If there is any change in the appropriate amount of exercise notified by the first notifying device 20 after a plurality of dialysis-treatment sessions, the exercise prescription can be reviewed appropriately.

The second calculating device 21 calculates the difference or ratio between the circulating-blood-volume rate of change (ΔBV) (the parameter regarding changes in circulating blood volume) or the blood pressure (the parameter regarding the vital sign) of the particular patient that is measured while the exercise is taken during the current blood purification treatment (dialysis treatment) and the circulating-blood-volume rate of change (ΔBV) or the blood pressure that is stored in the storage device 18. For example, as illustrated in FIG. 13, as the circulating-blood-volume rate of change (ΔBV) measured during the current blood purification treatment deviates from the circulating-blood-volume rate of change (α1 or α2) measured during the past blood purification treatment, the difference or ratio calculated by the second calculating device 21 increases.

The second monitoring device 22 monitors whether or not the difference or ratio calculated by the second calculating device 21 is over a predetermined threshold. For example, in the case illustrated in FIG. 13, compared with the reduction in the circulating-blood-volume rate of change (ΔBV) after the exercise start time T1 in the past blood purification treatment, the reduction in the circulating-blood-volume rate of change (ΔBV) after the exercise start time T1 in the current treatment tends to be small. Therefore, the difference or ratio calculated by the second calculating device 21 becomes large and goes over the predetermined threshold.

If the difference or ratio calculated by the second calculating device 21 is judged by the second monitoring device 22 to be over the predetermined threshold, the second judging device 23 then judges whether the amount of exercise is insufficient or excessive for that patient. Accordingly, a notification for a change in the amount of exercise can be provided by the first notifying device 20. For example, in the case illustrated in FIG. 13, the amount of exercise is judged to be insufficient. Accordingly, a notification for increasing the amount of exercise (increasing the intensity of exercise stress) can be provided.

If the difference or ratio calculated by the second calculating device 21 is judged by the second monitoring device 22 to be over the predetermined threshold, whether or not the blood pressure is stable is then judged. Only if the blood pressure is judged to be stable, a notification for a change in the amount of exercise is provided by the first notifying device 20. For example, in the case illustrated in FIG. 14, the second calculating device 21 calculates the difference or ratio between the blood pressure of the particular patient that is measured while the exercise is taken during the current blood purification treatment (dialysis treatment) and the blood pressure stored in the storage device 18. If the difference is not over the predetermined threshold, the blood pressure can be judged to be stable.

In the present embodiment, the parameter regarding changes in circulating blood volume of the particular patient that is measured while the exercise is taken during the blood purification treatment is the circulating-blood-volume rate of change ($\Delta BV$), and the parameter regarding the vital sign of the particular patient is the blood pressure. Alternatively, other kinds of parameters may be taken, respectively.

Furthermore, in the present embodiment, the storage device 18, the first determining device 19, the first notifying device 20, the second calculating device 21, the second monitoring device 22, and the second judging device 23 are provided outside the hemodialysis apparatus 1. Alternatively, some of or all of the foregoing elements may be included in the hemodialysis apparatus 1. In that case, the first notifying device 20 may be a display, a sound generating device, or the like included in the hemodialysis apparatus 1.

Now, a third embodiment of the present invention will be described.

An exercise support apparatus according to the present embodiment is capable of supporting exercise taken by a patient during blood purification treatment as with the cases of the first and second embodiments and includes, as illustrated in FIG. 16, an exercise device S, a first input device W, a storage device 18, a first determining device 19, a first notifying device 20, a second calculating device 21, a second monitoring device 22, a second judging device 23, and a detection device E. The detection device E includes an electrocardiograph 24, a pulse oximeter 25, a blood flowmeter 26, and a body composition monitor 27. Elements that are the same as those described in the first or second embodiment are denoted by corresponding ones of the reference numerals, and detailed description of such elements is omitted.

The detection device E is provided for detecting parameters regarding vital signs of a particular patient that are acquired while the exercise is taken during blood purification treatment. Specifically, the electrocardiograph 24 is provided for detecting the action potential or the action current of cardiac muscle that is generated with the pulsation of the heart. The pulse oximeter 25 is provided for detecting the pulse rate and the percutaneous arterial oxygen saturation (SpO2) with a probe attached to a fingertip, an ear, or the like. The blood flowmeter 26 is provided for detecting the speed, the volume, and the like of the blood flow. The body composition monitor 27 measures various values regarding body composition, such as body fat, basal metabolic rate, muscle mass, and the like, and is capable of estimating values regarding body composition by, for example, supplying a very weak current to the body of the patient and measuring the electrical resistance.

In the present embodiment, the storage device 18 stores the parameter regarding the vital sign of the particular patient that is acquired by the electrocardiograph 24, the pulse oximeter 25, the blood flowmeter 26, or the body composition monitor 27; the perceived exertion experienced by the patient during the exercise; and the amount of exercise. On the basis of the parameter, the amount of exercise, and the perceived exertion experienced by the patient that are stored in the storage device 18, the first determining device 19 can determine an appropriate amount of exercise for the particular patient, and the first notifying device 20 can notify the appropriate amount of exercise for the particular patient that is determined by the first determining device 19.

In the present embodiment, as illustrated in FIG. 17, the second calculating device 21 calculates the difference or ratio between a cardiac output (a parameter regarding a vital sign) of the particular patient that is measured by the detection device E while the exercise is taken during the current blood purification treatment and cardiac outputs ($\alpha 1$ and $\alpha 2$) stored in the storage device 18. Furthermore, the second monitoring device 22 monitors whether or not the difference or ratio calculated by the second calculating device 21 is over a predetermined threshold. Furthermore, if the difference or ratio calculated by the second calculating device 21 is judged by the second monitoring device 22 to be over the predetermined threshold, a notification for a change in the amount of exercise can be provided.

Furthermore, in the present embodiment, as illustrated in FIG. 18, the second calculating device 21 calculates the difference or ratio between a heart rate (a parameter regarding another vital sign) of the particular patient that is measured by the detection device E while the exercise is taken during the current blood purification treatment and heart rates ($\alpha 1$ and $\alpha 2$) stored in the storage device 18. Furthermore, the second monitoring device 22 monitors whether or not the difference or ratio calculated by the second calculating device 21 is over a predetermined threshold. Furthermore, if the difference or ratio calculated by the second calculating device 21 is judged by the second monitoring device 22 to be over the predetermined threshold, a notification for a change in the amount of exercise can be provided.

Furthermore, in the present embodiment, as illustrated in FIG. 19, the second calculating device 21 calculates the difference or ratio between an oxygen uptake (a parameter regarding yet another vital sign) that is measured by the detection device E while the exercise is taken during the current blood purification treatment and oxygen uptakes ($\alpha 1$ and $\alpha 2$) stored in the storage device 18. Furthermore, the second monitoring device 22 monitors whether or not the difference or ratio calculated by the second calculating device 21 is over a predetermined threshold. Furthermore, if the difference or ratio calculated by the second calculating device 21 is judged by the second monitoring device 22 to be over the predetermined threshold, a notification for a change in the amount of exercise can be provided.

In the present embodiment, the storage device 18, the first determining device 19, the first notifying device 20, the second calculating device 21, the second monitoring device 22, and the second judging device 23 are provided outside the hemodialysis apparatus 1. Alternatively, some of or all of the foregoing elements may be included in the hemodialysis apparatus 1. In that case, the first notifying device 20 may be a display, a sound generating device, or the like included in the hemodialysis apparatus 1. Furthermore, while the detection device E is provided outside the hemodialysis apparatus 1, some of or all of the elements included in the detection device E may be included in the hemodialysis apparatus 1.

According to each of the second and third embodiments, the exercise support apparatus includes the storage device 18 that stores the parameter regarding changes in circulating blood volume of a particular patient or the parameter regarding the vital sign of the particular patient that is acquired while the exercise is taken during the blood purification treatment, the perceived exertion experienced by the patient during the exercise, and the amount of exercise; the first determining device 19 that determines an appropriate amount of exercise for the particular patient from the parameter, the amount of exercise, and the perceived exertion experienced by the patient that are stored in the storage device 18; and the first notifying device 20 that notifies the appropriate amount of exercise for the particular patient that is determined by the first determining device 19. Therefore, exercise that is safer and more suitable for the particular patient can be offered during blood purification treatment.

The exercise support apparatus further includes the second calculating device 21 that calculates the difference or ratio between the parameter regarding changes in circulating blood volume or the parameter regarding the vital sign of the particular patient that is measured while the exercise is taken during the current blood purification treatment and the parameter regarding changes in circulating blood volume or the parameter regarding the vital sign that is stored in the storage device 18; and the second monitoring device 22 that monitors whether or not the difference or ratio calculated by the second calculating device 21 is over a predetermined threshold. Therefore, the safety during exercise can further be increased.

Furthermore, if the difference or ratio calculated by the second calculating device 21 is judged by the second monitoring device 22 to be over the predetermined threshold, a notification for a change in the amount of exercise is provided. Therefore, the notification helps assuredly grasp the change in the amount of exercise, and the safety can be increased.

In particular, according to the second embodiment, the parameter regarding changes in circulating blood volume of the patient is the circulating-blood-volume rate of change that is measurable continuously during the blood purification treatment. Therefore, the monitoring by the second monitoring device can be performed in accordance with the circulating-blood-volume rate of change that is detectable in real time. Furthermore, according to the second embodiment, the parameter to be stored in the storage device 18 is detected by the sensor (the blood volume meter 2 or the blood pressure monitor 3) included in the blood purification apparatus intended for blood purification treatment. Therefore, the storing by the storage device can be performed by using the sensor intended for treatment. According to the third embodiment, the exercise support apparatus further includes the detection device E for detecting the parameter regarding the vital sign of the patient. Therefore, the appropriate amount of exercise for the particular patient that is determined by the first determining device 19 can be grasped more accurately.

While the exercise support apparatuses according to the second and third embodiments have been described above, the present invention is not limited thereto. For example, in the second embodiment, the parameter regarding changes in circulating blood volume of the patient is the circulating-blood-volume rate of change. Alternatively or in addition, plasma refilling rate (PRR) that is measurable continuously during the blood purification treatment may be taken. The plasma refilling rate (PRR) is calculable by using the blood volume meter 2 of the hemodialysis apparatus 1 and in accordance with the following arithmetic expression, assuming that the circulating blood volume of the patient is $\frac{1}{13}$ of the body weight before the treatment.

PRR=(Ultrafiltration volume during measurement period+Increment in circulating blood volume during measurement period)/Duration of measurement period Increment in circulating blood volume during measurement period=Circulating blood volume×Rate of change in ΔBV during measurement period Circulating blood volume=Body weight before treatment/13

If the plasma refilling rate (PRR) is taken as the parameter regarding changes in circulating blood volume of the patient, not only can the appropriate amount of exercise for the particular patient be notified by the first notifying device 20, but plasma refilling rates (α1 and α2), illustrated in FIG. 15, of the particular patient that have been measured while the exercise has been taken during the past blood purification treatment (dialysis treatment) can also be stored in the storage device 18. Then, the difference or ratio between the stored data and the plasma refilling rate (α1 and α2) of the particular patient that is measured while the exercise is taken during the current blood purification treatment (dialysis treatment) can be calculated by the second calculating device 21.

In such a case, the monitoring by the second monitoring device 22 and the judgement of providing the notification for a change in the amount of exercise by the second judging device 23 are performed in the same manner as in the above embodiments. In addition, the second monitoring device 22 can perform monitoring in accordance with the plasma refilling rate that is detectable in real time. While the present embodiment concerns a case where the present invention is applied to the hemodialysis apparatus 1 intended for hemodialysis treatment, the present invention may alternatively be applied to a blood purification apparatus intended for another kind of blood purification treatment.

Now, a fourth embodiment of the present invention will be described.

An exercise support apparatus according to the fourth embodiment is capable of supporting exercise taken by a patient during blood purification treatment and includes, as illustrated in FIG. 20, a blood volume meter 2 and a blood pressure monitor 3 that are included in a hemodialysis apparatus 1 intended for blood purification treatment (dialysis treatment), an exercise device S, a second input device 28, a second determining device 29, a second notifying device 30, and a third monitoring device 31. Elements that are the same as those described in any of the first to third embodiments are denoted by corresponding ones of the reference numerals, and detailed description of such elements is omitted.

The exercise support apparatus according to the present embodiment includes the second input device 28 electrically connected to the blood volume meter 2 and to the blood pressure monitor 3, the second determining device 29, the second notifying device 30, and the third monitoring device 31. The second input device 28 is a device to which parameters indicating the circulatory dynamics of the patient that are acquired after the blood purification treatment (hemodialysis treatment) is started are inputtable. In the present embodiment, the circulating-blood-volume rate of change (ΔBV) (the parameter regarding changes in circulating blood volume) of the patient that is measured by the blood volume meter 2, and the blood pressure (the parameter regarding the vital sign) of the patient that is measured by the blood pressure monitor 3 are inputted to the second input device 28.

The second determining device 29 determines that the parameter (the circulating-blood-volume rate of change (ΔBV) or the blood pressure) inputted to the second input device 28 is stabilized. Specifically, if the parameter inputted to the second input device 28 or the rate of change in the parameter follows a course that is continuously within a predetermined range, the second determining device 29 determines that the parameter is stabilized. Accordingly, the second notifying device 30 can notify the timing of starting the exercise.

For example, suppose that the parameter indicating the circulatory dynamics of the patient that is inputted to the second input device 28 is the circulating-blood-volume rate of change (ΔBV). As illustrated in FIG. 21, if the rate of change a in the circulating-blood-volume rate of change (ΔBV) follows a course that is continuously within a predetermined range D, it can be determined that the circulating-blood-volume rate of change (ΔBV) is stabilized. In contrast, as illustrated in FIG. 22, if the rate of change a in the circulating-blood-volume rate of change (ΔBV) does not follow a course that is continuously within the predetermined range D, it can be determined that the circulating-blood-volume rate of change (ΔBV) is not stabilized.

The second notifying device 30 is capable of notifying the timing of starting the exercise for each session of the blood purification treatment in accordance with the state of the patient or the state of the treatment. In the present embodiment, the second notifying device 30 is capable of notifying the timing of starting the exercise in accordance with the determination made by the second determining device 29. That is, if the parameter inputted to the second input device 28 is determined by the second determining device 29 to be stabilized, the second notifying device 30 notifies that the exercise may be started. The second notifying device 30 may be in any form such as a display that indicates the timing of starting the exercise, an informing device that informs the timing of starting the exercise with a voice sound, or the like.

The third monitoring device 31 is provided for monitoring the state of the patient or another parameter (such as blood pressure) if the parameter (such as the circulating-blood-volume rate of change (ΔBV)) inputted to the second input device 28 is determined by the second determining device 29 to be not stabilized. Therefore, changes in the condition of the patient or another like situation that may occur when the parameter inputted to the second input device 28 is not stabilized can be monitored, and the safety can be provided.

Now, a control process according to the present embodiment will be described.

As illustrated in FIG. 23, first in step S1, the second determining device 29 determines whether or not the rate of change in the circulating-blood-volume rate of change (ΔBV) is stable. If, for example, the course illustrated in FIG. 21 is acquired, the parameter is determined to be stable. Then, the process proceeds to step S2, where the second notifying device 30 notifies the timing of starting the exercise. The determination in step S1 that the parameter is stabilized may alternatively be made if the circulating-blood-volume rate of change (ΔBV) is below a predetermined threshold.

In step S1, if the circulating-blood-volume rate of change (ΔBV) or the rate of change in the circulating-blood-volume rate of change (ΔBV) follows, for example, the course illustrated in FIG. 22, the second determining device 29 determines that the parameter is not stable. Then, the process proceeds to step S3, where the third monitoring device 31 starts monitoring (monitoring of the state of the patient or another parameter). Furthermore, in step S4, it is determined that the timing of starting the exercise is not notified.

If the parameter indicating the circulatory dynamics of the patient that is inputted to the second input device 28 is the blood pressure, another control process illustrated in FIG. 24 is performed. In this process, in step S1, whether or not the blood pressure (including systolic pressure, diastolic pressure, mean blood pressure, pulse, and the like) measured by the blood pressure monitor 3 is reduced from the blood pressure measured before the treatment is started is determined. If it is determined that the blood pressure is reduced, whether or not the extent of the reduction in the blood pressure is within a stable range is determined in step S2.

If it is determined in step S2 that the extent of the reduction in the blood pressure is within the stable range, the process proceeds to step S3, where the second notifying device 30 notifies the timing of starting the exercise. If it is determined in step S2 that the extent of the reduction in the blood pressure is out of the stable range (for example, a reduction by 100 mmHg or greater from the blood pressure at rest), it is determined in step S5 that the timing of starting the exercise is not notified. In contrast, if it is determined in step S1 that the blood pressure measured by the blood pressure monitor 3 is not reduced from the blood pressure measured before the treatment is started, the process proceeds to step S4, where the third monitoring device 31 starts monitoring (monitoring of the state of the patient or another parameter). Furthermore, it is determined in step S5 that the timing of starting the exercise is not notified.

In the present embodiment, among the parameters indicating the circulatory dynamics of the patient that are inputted to the second input device 28, the circulating-blood-volume rate of change (ΔBV) is taken as the parameter regarding changes in circulating blood volume of the patient, and the blood pressure is taken as the parameter regarding the vital sign of the patient. Alternatively, other parameters may be taken, respectively.

In the present embodiment, the second input device 28, the second determining device 29, the second notifying device 30, and the third monitoring device 31 are provided outside the hemodialysis apparatus 1. Alternatively, some of or all of the foregoing elements may be included in the hemodialysis apparatus 1. In that case, the second notifying device 30 may be a display, a sound generating device, or the like included in the hemodialysis apparatus 1.

Now, a fifth embodiment of the present invention will be described.

An exercise support apparatus according to the fifth embodiment is capable of supporting exercise taken by a patient during blood purification treatment as with the cases of the first to fourth embodiments and includes, as illustrated in FIG. 25, an exercise device S, a second input device 28, a second determining device 29, a second notifying device 30, a third monitoring device 31, and a detection device E. The detection device E includes an electrocardiograph 24, a pulse oximeter 25, a blood flowmeter 26, and a body composition monitor 27. Elements that are the same as those described in any of the first to fourth embodiments are denoted by corresponding ones of the reference numerals, and detailed description of such elements is omitted.

In the present embodiment, a parameter regarding a vital sign of a particular patient that is acquired by the electrocardiograph 24, the pulse oximeter 25, the blood flowmeter 26, or the body composition monitor 27 is inputtable to the second input device 28 as the parameter indicating the circulatory dynamics of the patient. If it is determined by the second determining device 29 that the inputted parameter is stabilized, the second notifying device 30 can notify the timing of starting the exercise.

For example, if the parameter indicating the circulatory dynamics of the patient that is inputted to the second input device 28 is the heart rate (or the respiration rate), a control process illustrated in FIG. 26 is performed. In this process, in step S1, whether or not the heart rate is stabilized after increasing for a specific period of time is determined. If it is determined that the heart rate is stabilized after increasing for the specific period of time, the process proceeds to step S2, where the second notifying device 30 notifies the timing of starting the exercise. In contrast, in step S1, if it is determined that the heart rate does not increase before the specific period of time elapses or the heart rate is not stabilized even after increasing for the specific period of time, the process proceeds to step S3.

In step S3, the third monitoring device 31 starts monitoring (monitoring of the state of the patient or another parameter). Furthermore, in step S4, it is determined that the timing of starting the exercise is not notified. If the heart rate does not increase even after ultrafiltration is started, the timing of starting the exercise may be determined in combination with another parameter. If the heart rate is increased or decreased significantly after the specific period of time and if there is any occurrence of an obvious ST-T wave change (such as a change indicating myocardial ischemia), paroxysmal atrial fibrillation, frequent ventricular extrasystole, RonT ventricular extrasystole, ventricular tachycardia, or the like, it is preferably determined that the timing of starting the exercise is not notified.

If the parameter indicating the circulatory dynamics of the patient that is inputted to the second input device 28 is, for example, oxygen saturation (or pulse-wave amplitude, which is considered to reflect the state of circulation in peripheral part), a control process illustrated in FIG. 27 is performed. In this process, in step S1, whether or not the oxygen saturation is stabilized after increasing for a specific period of time is determined. If it is determined that the oxygen saturation is stabilized after increasing for the specific period of time, the process proceeds to step S2, where the second notifying device 30 notifies the timing of starting the exercise.

In contrast, in step S1, if it is determined that the oxygen saturation does not increase before the specific period of time elapses or the oxygen saturation is not stabilized even after increasing for the specific period of time, the process proceeds to step S3, where the third monitoring device 31 starts monitoring (monitoring of the state of the patient or another parameter). Furthermore, in step S4, it is determined that the timing of starting the exercise is not notified. Performing ultrafiltration tends to reduce the pulse-wave amplitude. Therefore, the timing of starting the exercise may be notified when the pulse-wave amplitude goes below a specific value.

Now, a sixth embodiment of the present invention will be described.

An exercise support apparatus according to the present embodiment is capable of supporting exercise taken by a patient during blood purification treatment as with the cases of the first to fifth embodiments and includes, as illustrated in FIG. 28, an exercise device S, a second input device 28, a second determining device 29, a second notifying device 30, and a third monitoring device 31. The second input device 28 is electrically connected to a dialysis dose monitor 32 included in a hemodialysis apparatus 1. Elements that are the same as those described in any of the first to fifth embodiments are denoted by corresponding ones of the reference numerals, and detailed description of such elements is omitted.

The dialysis dose monitor 32 is provided to the dialysate drain line L2 (see FIG. 3) of the dialysis-apparatus body 14 and is capable of monitoring Kt/V (standardized dialysis dose) by detecting the concentration of waste liquid (for example, the concentration of urine in the waste liquid) drained from the dialyzer 11 while blood purification treatment is conducted. The value of Kt/V is calculable in accordance with the following arithmetic expression.

Standardized dialysis dose $(Kt/V) = -\ln(C(e)/C(s) - 0.008t) + (4 - 3.5 \times C(e)/C(s)) \times (VUF/DVV)$ where $C(s)$ denotes urea nitrogen concentration (initial value) at the start of hemodialysis treatment, $C(e)$ denotes the current urea nitrogen concentration (at a point during monitoring), VUF denotes ultrafiltration volume, DW denotes the dry weight of the patient, K denotes clearance, t denotes the duration of dialysis treatment, and V denotes urea distribution volume.

In the present embodiment, the waste-liquid concentration acquired by the dialysis dose monitor 32 is inputtable to the second input device 28 as a parameter indicating the state of the treatment. If it is determined by the second determining device 29 that the inputted parameter is stabilized, the second notifying device 30 can notify the timing of starting the exercise. For example, as illustrated in FIG. 29, if the waste-liquid concentration measured by the dialysis dose monitor 32 follows a course that is continuously within a predetermined range D (particularly in the present embodiment, if the change in the concentration is within the predetermined range D during a period from time T1 to time T2), it is determined by the second determining device 29 that the parameter is stabilized. In contrast, as illustrated in FIG. 30, if the waste-liquid concentration does not follow a course that is continuously within the predetermined range D (particularly in the present embodiment, if the change in the concentration is not within the predetermined range during the period from time T1 to time T2), it is determined by the second determining device 29 that the parameter is not stabilized.

According to each of the fourth to sixth embodiments, the exercise support apparatus includes the second notifying device 30 capable of notifying the timing of starting the exercise for each session of the blood purification treatment in accordance with the state of the patient or the state of the treatment. Therefore, the exercise during the blood purification treatment can be started at an appropriate timing in accordance with the state of the patient or the state of the treatment. In particular, according to each of the fourth and fifth embodiments, the exercise support apparatus includes the second input device 28 to which the parameter indicating the circulatory dynamics of the patient that is acquired after the blood purification treatment is started is inputtable, and the second determining device 29 that determines that the parameter inputted to the second input device 28 is stabilized. Furthermore, the second notifying device 30 is capable of notifying the timing of starting the exercise in accordance with the determination made by the second determining device 29. Therefore, the exercise can be started at a more appropriate timing.

In each of the relevant embodiments, if the parameter inputted to the second input device 28 or the rate of change in the parameter follows a course that is continuously within a predetermined range, the parameter is determined by the second determining device 29 to be stabilized. Then, the second notifying device 30 can notify the timing of starting the exercise. Therefore, the timing of starting the exercise can be notified accurately. Furthermore, the parameter to be inputted to the second input device 28 is the parameter regarding changes in circulating blood volume of the patient (such as the circulating-blood-volume rate of change (ΔBV)), the parameter regarding the vital sign of the patient (such as the blood pressure), or a parameter regarding the blood purification treatment (such as the waste-liquid concentration). Therefore, the timing of starting the exercise can be notified more accurately.

According to each of the fourth and sixth embodiments, the parameter to be inputted to the second input device 28 is detected by the sensor (such as the blood volume meter 2, the blood pressure monitor 3, the dialysate monitor 20, or the like) included in the blood purification apparatus intended for blood purification treatment. Therefore, the timing of starting the exercise can be notified by using the sensor intended for treatment. Furthermore, according to the fifth embodiment, the exercise support apparatus includes the detection device E for detecting the parameter regarding the vital sign of the patient. Therefore, when the timing of starting the exercise is notified, the state of the patient can be grasped more accurately.

While the exercise support apparatuses according to the respective embodiments have been described above, the present invention is not limited thereto. For example, in the fourth embodiment, the parameter regarding changes in circulating blood volume of the patient is the circulating-blood-volume rate of change. Alternatively or in addition, plasma refilling rate (PRR) that is measurable continuously during the blood purification treatment may be taken. The plasma refilling rate (PRR) is calculable by using the blood volume meter 2 included in the hemodialysis apparatus 1 and in accordance with the following arithmetic expression, assuming that the circulating blood volume of the patient is ⅟₁₃ of the body weight before the treatment.

PRR=(Ultrafiltration volume during measurement period+Increment in circulating blood volume during measurement period)/Duration of measurement period Increment in circulating blood volume during measurement period=Circulating blood volume×Rate of change in ΔBV during measurement period Circulating blood volume=Body weight before treatment/13

Suppose that the plasma refilling rate (PRR) is inputted to the second input device 28 as the parameter regarding changes in the circulating blood volume of the patient. In such a case, if it is determined by the second determining device 29 that the inputted plasma refilling rate (PRR) is stabilized, the second notifying device 30 notifies the timing of starting the exercise.

To allow the second notifying device 30 to notify the timing of starting the exercise, the state of the patient or the state of the treatment only needs to satisfy a predetermined condition. The condition to be satisfied may be based on, for example, an image of the patient that is taken by a camera, the temperature of the patient that is measured by a thermometer, or the sweat rate of the patient that is measured by a sensor. While the above embodiments concerns a case where the present invention is applied to the hemodialysis apparatus 1 intended for hemodialysis treatment, the present invention may alternatively be applied to a blood purification apparatus intended for another kind of blood purification treatment.

The present invention is applicable to any exercise support apparatus having additional functions or the like, as long as the apparatus includes an estimation-line-generating device that generates an estimation line representing a course of a parameter regarding changes in circulating blood volume of the patient that is estimated to be observed after the exercise is started, the estimation line being generated after the blood purification treatment is started and from a continuous measurement of the parameter regarding changes in circulating blood volume that is conducted before the exercise is started; a first calculating device that calculates a difference or ratio between a measured value of the parameter regarding changes in circulating blood volume of the patient that is acquired after the exercise during the blood purification treatment is started and a value of the estimation line generated by the estimation-line-generating device; and a first monitoring device that monitors whether or not the difference or ratio calculated by the first calculating device is over a predetermined threshold.

REFERENCE SIGNS LIST

1 hemodialysis apparatus (blood purification apparatus)
2 blood volume meter
3 blood pressure monitor
4 estimation-line-generating device
5 first calculating device
6 first monitoring device
7 informing device
8 comparing device
9 first judging device
10 blood circuit
11 dialyzer
12 blood pump
13 air trap chamber
14 dialysis-apparatus body
15 dialysate supply device
16 ultrafiltration pump
17 hematocrit sensor
18 storage device
19 first determining device
20 first notifying device
21 second calculating device
22 second monitoring device
23 second judging device
24 electrocardiograph
25 pulse oximeter
26 blood flowmeter
27 body composition monitor
28 second input device
29 second determining device
30 second notifying device
31 third monitoring device
32 dialysis dose monitor
S exercise device
W first input device
E detection device

The invention claimed is:

1. An exercise support apparatus capable of supporting exercise taken by a patient during blood purification treatment, the exercise support apparatus comprising:
    an estimation-line-generating device that generates an estimation line representing a course of a parameter regarding changes in circulating blood volume of the patient that is estimated to be observed after the exercise is started, the estimation line being gene rated after the blood purification treatment is started and from a continuous measurement of the parameter regarding changes in circulating blood volume that is conducted before the exercise is started;
    a first calculating device that calculates a difference or ratio between a measured value of the parameter regarding changes in circulating blood volume of the patient that is acquired after the exercise during the blood purification treatment is started and a value of the estimation line generated by the estimation-line-generating device;

a first monitoring device that monitors whether or not the difference or ratio calculated by the first calculating device is over a predetermined threshold;

wherein if the difference or ratio calculated by the first calculating device is judged by the first monitoring device to be over the predetermined threshold, the exercise is configured to be stopped or information for stopping the exercise is provided; and an informing device that provides the information for stopping the exercise or is configured to stop the exercise;

wherein the informing device is configured to be in communication with an exercise device so that upon the first monitoring device indicating the predetermined threshold is exceeded the informing device is configured to forcibly stop the exercise device.

2. The exercise support apparatus according to claim 1, further comprising:

a comparing device that compares a tendency of changes in the difference or ratio calculated by the first calculating device during or after the exercise and an ideal tendency of changes in the difference or ratio; and a first judging device capable of judging whether or not the exercise taken during the blood purification treatment is an appropriate amount of exercise based on the comparison made by the comparing device.

3. The exercise support apparatus according to claim 2, wherein the first judging device is capable of initiating a measurement of blood pressure of the patient or providing information that urges the measurement of blood pressure in accordance with the comparison made by the comparing device.

4. The exercise support apparatus according to claim 1, wherein the parameter regarding changes in circulating blood volume of the patient is circulating-blood-volume rate of change that is measurable continuously during the blood purification treatment.

5. The exercise support apparatus according to claim 1, wherein the parameter regarding changes in circulating blood volume of the patient is plasma refilling rate that is measurable continuously during the blood purification treatment.

6. The exercise support apparatus according to claim 1, wherein the parameter regarding changes in circulating blood volume of the patient is detected by a sensor included in a blood purification apparatus intended for blood purification treatment.

7. The exercise support apparatus according to claim 1, further comprising:

a storage device that stores the parameter regarding changes in circulating blood volume of a particular patient or a parameter regarding a vital sign of the particular patient that is acquired while the exercise is taken during the blood purification treatment, perceived exertion experienced by the patient during the exercise, and an amount of exercise;

a first determining device that determines an appropriate amount of exercise for the particular patient from the parameter, the amount of exercise, and the perceived exertion experienced by the patient that are stored in the storage device; and a first notifying device that notifies the appropriate amount of exercise for the particular patient that is determined by the first determining device.

8. The exercise support apparatus according to claim 7, further comprising:

a second calculating device that calculates a difference or ratio between the parameter regarding changes in circulating blood volume or the parameter regarding the vital sign of the particular patient that is measured while the exercise is taken during a current blood purification treatment and the parameter regarding changes in circulating blood volume or the parameter regarding the vital sign that is stored in the storage device; and a second monitoring device that monitors whether or not the difference or ratio calculated by the second calculating device is over a predetermined threshold.

9. The exercise support apparatus according to claim 8, wherein if the difference or ratio calculated by the second calculating device is judged by the second monitoring device to be over the predetermined threshold, a notification for a change in the amount of exercise is provided.

10. The exercise support apparatus according to claim 7, wherein the parameter regarding changes in circulating blood volume of the patient is circulating-blood-volume rate of change that is measurable continuously during the blood purification treatment.

11. The exercise support apparatus according to claim 7, wherein the parameter to be stored in the storage device is detected by a sensor included in a blood purification apparatus intended for blood purification treatment.

12. The exercise support apparatus according to claim 7, further comprising a detection device for detecting the parameter regarding the vital sign of the patient.

13. The exercise support apparatus according to claim 1, further comprising a second notifying device capable of notifying a timing of starting the exercise for each session of the blood purification treatment in accordance with a state of the patient or a state of the treatment.

14. The exercise support apparatus according to claim 13, further comprising:

an input device to which a parameter indicating circulatory dynamics of the patient that is acquired after the blood purification treatment is started is inputtable; and a second determining device that determines that the parameter inputted to the input device is stabilized, wherein the second notifying device is capable of notifying the timing of starting the exercise in accordance with the determination made by the second determining device.

15. The exercise support apparatus according to claim 14, wherein if the parameter inputted to the input device or a rate of change in the parameter follows a course that is continuously within a predetermined range, the parameter is determined by the second determining device to be stabilized, and the second notifying device is allowed to notify the timing of starting the exercise.

16. The exercise support apparatus according to claim 14, wherein the parameter to be inputted to the input device is the parameter regarding changes in circulating blood volume of the patient, the parameter regarding the vital sign of the patient, or a parameter regarding the blood purification treatment.

17. The exercise support apparatus according to claim 14, wherein the parameter to be inputted to the input device is detected by a sensor included in a blood purification apparatus intended for blood purification treatment.

18. The exercise support apparatus according to claim 13, further comprising a detection device for detecting the parameter regarding the vital sign of the patient.

* * * * *